United States Patent
Chan et al.

(10) Patent No.: US 7,748,070 B2
(45) Date of Patent: Jul. 6, 2010

(54) ELECTRIC TOOTHBRUSH COMPRISING AN ELECTRICALLY POWERED ELEMENT

(75) Inventors: John Geoffrey Chan, Loveland, OH (US); Chanchal Kumar Ghosh, West Chester, OH (US); Stephen Andras Kovacs, Loveland, OH (US); Lowen Robert Morrision, Jr., Cincinnati, OH (US); Ping Wang, Beijing (CN); Aleksey Mikhailovich Pinyayev, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/191,370

(22) Filed: Aug. 14, 2008

(65) Prior Publication Data
US 2008/0301890 A1 Dec. 11, 2008

Related U.S. Application Data

(63) Continuation of application No. 10/888,206, filed on Jul. 9, 2004, now abandoned, which is a continuation-in-part of application No. 10/832,168, filed on Apr. 26, 2004, and a continuation-in-part of application No. 10/842,302, filed on May 10, 2004, now abandoned, and a continuation-in-part of application No. 10/847,429, filed on May 17, 2004, and a continuation-in-part of application No. 10/887,644, filed on Jul. 9, 2004, and a continuation-in-part of application No. 10/887,667, filed on Jul. 9, 2004, now abandoned.

(60) Provisional application No. 60/501,266, filed on Sep. 9, 2003.

(51) Int. Cl.
A46B 13/02 (2006.01)
A61C 17/20 (2006.01)
A61C 17/22 (2006.01)
A61C 17/34 (2006.01)

(52) U.S. Cl. .............................. 15/22.1; 15/28; 433/29; 433/119

(58) Field of Classification Search .................. 15/22.1, 15/22.2, 22.4, 23, 28; 433/29, 118, 119, 433/215, 216
See application file for complete search history.

(56) References Cited

U.S. PATENT DOCUMENTS 3,261,978 A 7/1966 Brenman (Continued)

FOREIGN PATENT DOCUMENTS

AU 200036442 3/2001

(Continued)

OTHER PUBLICATIONS

American Opto Plus LED Corp, Part No. L314NWC-15DS (spec sheet).

(Continued)

Primary Examiner—Mark Spisich

(57) ABSTRACT

An electric toothbrush having a handle, a head, and a neck extending between the handle and the head is disclosed. The handle has a hollow interior region having a motor and an electrical power source. The head includes an ultrasonic transducer and a bristle field. The ultrasonic transducer is in electrical communication with the electrical power source, and a shaft is operatively connected to the motor for moving the bristle field.

12 Claims, 29 Drawing Sheets

U.S. PATENT DOCUMENTS

| | | | |
|---|---|---|---|
| 3,309,274 A | 3/1967 | Brilliant |
| 3,524,088 A | 8/1970 | Ryckman, Jr. |
| 3,667,454 A | 6/1972 | Prince |
| 3,711,700 A | 1/1973 | Westlund |
| 3,732,416 A | 5/1973 | Audesse |
| 3,775,800 A | 12/1973 | Veneziani |
| 4,156,620 A | 5/1979 | Clemens |
| 4,266,535 A | 5/1981 | Moret |
| 4,290,433 A | 9/1981 | Alfano |
| RE31,815 E | 1/1985 | Albano |
| 4,515,476 A | 5/1985 | Ingmar |
| 4,578,033 A | 3/1986 | Mossle |
| 4,590,061 A | 5/1986 | Southard |
| 4,619,612 A | 10/1986 | Weber |
| 4,661,070 A | 4/1987 | Friedman |
| 4,779,173 A | 10/1988 | Carr |
| 4,826,431 A | 5/1989 | Fujimura |
| 4,827,550 A | 5/1989 | Graham |
| 4,840,563 A | 6/1989 | Altendorf |
| 4,845,795 A | 7/1989 | Crawford |
| 4,872,837 A | 10/1989 | Issalene |
| 4,968,249 A | 11/1990 | Lohn |
| 4,989,287 A | 2/1991 | Scherer |
| 5,030,090 A | 7/1991 | Maeda |
| 5,032,178 A | 7/1991 | Cornell |
| 5,033,150 A | 7/1991 | Gross |
| 5,123,845 A | 6/1992 | Vassiliadis |
| 5,160,194 A | 11/1992 | Feldman |
| 5,199,870 A | 4/1993 | Steiner |
| 5,226,206 A | 7/1993 | Davidovitz |
| 5,253,382 A | 10/1993 | Beny |
| 5,275,564 A | 1/1994 | Vassiliadis |
| 5,290,274 A | 3/1994 | Levy |
| 5,295,827 A | 3/1994 | Fundingsland |
| 5,306,143 A | 4/1994 | Levy |
| 5,337,435 A | 8/1994 | Krasner |
| 5,353,460 A | 10/1994 | Bauman |
| 5,359,747 A | 11/1994 | Amakasu |
| 5,429,120 A | 7/1995 | Lewitus |
| 5,435,724 A | 7/1995 | Goodman |
| 5,448,792 A | 9/1995 | Wiedemann |
| 5,501,599 A | 3/1996 | Rechmann |
| 5,504,959 A | 4/1996 | Yukawa |
| 5,617,601 A | 4/1997 | McDougall |
| 5,645,428 A | 7/1997 | Yarborough |
| 5,653,591 A | 8/1997 | Loge |
| 5,658,148 A | 8/1997 | Neuberger |
| 5,722,106 A | 3/1998 | Masterman |
| 5,766,011 A | 6/1998 | Sibner |
| 5,785,527 A | 7/1998 | Jensen |
| 5,800,165 A | 9/1998 | Kirsch |
| 5,813,855 A | 9/1998 | Crisio |
| 5,836,030 A | 11/1998 | Hazeu |
| 5,842,245 A | 12/1998 | Pai |
| 5,876,206 A | 3/1999 | Maurer |
| 5,879,159 A | 3/1999 | Cipolla |
| 5,894,620 A | 4/1999 | Polaert |
| 5,896,614 A | 4/1999 | Flewitt |
| 5,921,251 A | 7/1999 | Joshi |
| 5,957,687 A | 9/1999 | Brilliant |
| 6,000,083 A | 12/1999 | Blaustein |
| 6,026,828 A | 2/2000 | Altshuler |
| 6,056,548 A | 5/2000 | Neuberger |
| 6,086,363 A | 7/2000 | Moran |
| 6,094,767 A | 8/2000 | Imura |
| D432,312 S | 10/2000 | Blaustein |
| 6,129,721 A | 10/2000 | Kataoka |
| 6,135,774 A | 10/2000 | Hack |
| 6,139,320 A | 10/2000 | Hahn |
| D433,814 S | 11/2000 | Blaustein |
| 6,162,055 A | 12/2000 | Montgomery |
| 6,178,579 B1 | 1/2001 | Blaustein |
| 6,189,693 B1 | 2/2001 | Blaustein |
| 6,202,242 B1 | 3/2001 | D'Miles |
| 6,231,338 B1 | 5/2001 | DeJosselin de Jong |
| 6,231,343 B1 | 5/2001 | Ishibashi |
| 6,237,178 B1 | 5/2001 | Krammer |
| 6,251,127 B1 | 6/2001 | Biel |
| 6,291,568 B1 | 9/2001 | Lussey |
| 6,311,837 B1 | 11/2001 | Blaustein |
| 6,314,605 B1 | 11/2001 | Solanki |
| 6,325,623 B1 | 12/2001 | Melnyk |
| 6,343,400 B1 | 2/2002 | Massholder |
| 6,343,933 B1 | 2/2002 | Montgomery |
| 6,358,272 B1 | 3/2002 | Wilden |
| 6,360,395 B2 | 3/2002 | Blaustein |
| 6,371,294 B1 | 4/2002 | Blaustein |
| D456,998 S | 5/2002 | Blaustein |
| D457,728 S | 5/2002 | Blaustein |
| D458,030 S | 6/2002 | Blaustein |
| D458,455 S | 6/2002 | Blaustein |
| D459,584 S | 7/2002 | Blaustein |
| D459,894 S | 7/2002 | Blaustein |
| D459,895 S | 7/2002 | Blaustein |
| 6,416,319 B1 | 7/2002 | Cipolla |
| 6,417,917 B1 | 7/2002 | Jung |
| D461,642 S | 8/2002 | Blaustein |
| 6,439,888 B1 | 8/2002 | Boutoussov |
| D465,088 S | 11/2002 | Blaustein |
| 6,485,300 B1 | 11/2002 | Muller |
| 6,546,585 B1 | 4/2003 | Blaustein |
| 6,561,802 B2 | 5/2003 | Alexander |
| 6,561,808 B2 | 5/2003 | Neuberger |
| 6,564,940 B2 | 5/2003 | Blaustein |
| 6,581,233 B1 | 6/2003 | Cheng |
| D476,486 S | 7/2003 | Whitney |
| 6,597,934 B1 | 7/2003 | DeJong |
| 6,602,073 B2 | 8/2003 | Schilling |
| 6,616,450 B2 | 9/2003 | Mossle |
| 6,616,451 B1 | 9/2003 | Rizolu |
| D483,182 S | 12/2003 | Blaustein |
| 6,685,471 B1 | 2/2004 | Kawamura |
| 6,702,576 B2 | 3/2004 | Fischer |
| 6,752,627 B2 | 6/2004 | Lin |
| 6,783,363 B2 | 8/2004 | Eguchi |
| 6,843,981 B1 | 1/2005 | Ishibashi |
| 6,893,259 B1 | 5/2005 | Reizenson |
| 6,902,397 B2 | 6/2005 | Farrell |
| 6,957,907 B2 | 10/2005 | Fischer |
| 7,024,717 B2 | 4/2006 | Hilscher |
| 7,033,381 B2 | 4/2006 | Larsen |
| 7,240,390 B2 | 7/2007 | Pfenniger |
| 2001/0022277 A1 | 9/2001 | Blaustein |
| 2002/0014862 A1 | 2/2002 | Fregoso |
| 2002/0020645 A1 | 2/2002 | Blaustein |
| 2002/0029988 A1 | 3/2002 | Blaustein |
| 2002/0032941 A1 | 3/2002 | Blaustein |
| 2002/0078514 A1 | 6/2002 | Blaustein |
| 2002/0119100 A1 | 8/2002 | Okada |
| 2002/0162180 A1 | 11/2002 | Blaustein |
| 2002/0182563 A1 | 12/2002 | Boutoussov |
| 2002/0187455 A1 | 12/2002 | Melikechi |
| 2003/0022126 A1 | 1/2003 | Buchalla et al. |
| 2003/0036031 A1 | 2/2003 | Lieb |
| 2003/0059738 A1 | 3/2003 | Neuberger |
| 2003/0076281 A1 | 4/2003 | Morgan |
| 2003/0079305 A1 | 5/2003 | Daisuke |
| 2003/0097122 A1 | 5/2003 | Ganz |
| 2003/0104340 A1 | 6/2003 | Clemans |
| 2003/0140435 A1 | 7/2003 | Eliav |
| 2003/0143510 A1 | 7/2003 | Berube-Lauziere |
| 2003/0163881 A1 | 9/2003 | Driesen |
| 2003/0198605 A1 | 10/2003 | Montgomery |
| 2003/0226223 A1 | 12/2003 | Chan |

| | | | | | | |
|---|---|---|---|---|---|---|
| 2004/0019990 | A1 | 2/2004 | Farrell | DE | 10115426 | 10/2002 |
| 2004/0023184 | A1 | 2/2004 | De Josselin de Jong | DE | 20214259 | 11/2002 |
| 2004/0047816 | A1 | 3/2004 | Yamaguchi | DE | 20307294 | 11/2003 |
| 2004/0106081 | A1 | 6/2004 | Karazivan | DE | 10304221 | 8/2004 |
| 2004/0109829 | A1 | 6/2004 | Nonami | DE | 20319405 | 4/2005 |
| 2004/0138082 | A1 | 7/2004 | Sugihara | DE | 202004001004 | 4/2005 |
| 2004/0170578 | A1 | 9/2004 | Sugihara | DE | 10347258 | 5/2005 |
| 2004/0171505 | A1 | 9/2004 | Nonami | DE | 202005002341 | 7/2005 |
| 2004/0180008 | A1 | 9/2004 | Yamaguchi | DE | 202005015767 | 2/2006 |
| 2004/0191729 | A1 | 9/2004 | Altshuler | DE | 202005018891 | 6/2006 |
| 2004/0193235 | A1 | 9/2004 | Altshuler | DE | 202005019681 | 6/2006 |
| 2004/0193236 | A1 | 9/2004 | Altshuler | EP | 0 054043 | 12/1981 |
| 2004/0199227 | A1 | 10/2004 | Altshuler | EP | 0 056 877 | 8/1982 |
| 2004/0204745 | A1 | 10/2004 | Altshuler | EP | 0 138 119 | 10/1986 |
| 2004/0210276 | A1 | 10/2004 | Altshuler | EP | 0 238 778 | 9/1987 |
| 2004/0230186 | A1 | 11/2004 | Obrebski | EP | 0 278 855 | 10/1989 |
| 2005/0048434 | A1 | 3/2005 | Cipolla | EP | 0 406 454 | 1/1991 |
| 2005/0050658 | A1 | 3/2005 | Chan | EP | 0 417 963 | 3/1991 |
| 2005/0050659 | A1 | 3/2005 | Chan | EP | 0 516 872 | 12/1992 |
| 2005/0053895 | A1 | 3/2005 | Pinyayev | EP | 0 530 646 | 3/1993 |
| 2005/0053896 | A1 | 3/2005 | Pinyayev | EP | 0 637 976 | 11/1993 |
| 2005/0053898 | A1 | 3/2005 | Ghosh | EP | 0 575 274 | 12/1993 |
| 2005/0064370 | A1 | 3/2005 | Duret | EP | 0 527 163 | 1/1994 |
| 2005/0064371 | A1 | 3/2005 | Soukos | EP | 0 593 375 | 4/1994 |
| 2005/0066459 | A1 | 3/2005 | Pinyayev | EP | 0 637 438 | 2/1995 |
| 2005/0074723 | A1 | 4/2005 | Ostler | EP | 0 651 978 | 5/1995 |
| 2005/0170310 | A1 | 8/2005 | Schafer | EP | 0 672 387 | 9/1995 |
| 2005/0170316 | A1 | 8/2005 | Russell | EP | 0 714 632 | 6/1996 |
| 2005/0256554 | A1 | 11/2005 | Malak | EP | 0 743 029 | 11/1996 |
| 2005/0265933 | A1 | 12/2005 | Montgomery | EP | 0 914 808 | 5/1999 |
| 2005/0271997 | A1 | 12/2005 | Mikami | EP | 0 914 809 | 5/1999 |
| 2005/0274906 | A1 | 12/2005 | Riddell | EP | 0 927 544 | 7/1999 |
| 2006/0008767 | A1 | 1/2006 | Whalen | EP | 0 973 460 | 1/2000 |
| 2006/0048696 | A1 | 3/2006 | Yamazaki | EP | 1 025 776 | 8/2000 |
| 2006/0110700 | A1 | 5/2006 | Cipolla | EP | 1 048 291 | 11/2000 |
| 2006/0257822 | A1 | 11/2006 | Ghosh | EP | 1 083 806 | 3/2001 |
| 2007/0298370 | A1 | 12/2007 | Pinyayev | EP | 1 101 436 | 5/2001 |
| 2007/0298371 | A1 | 12/2007 | Pinyayev | EP | 1 118 311 | 7/2001 |
| 2007/0298372 | A1 | 12/2007 | Pinyayev | EP | 1 138 275 | 10/2001 |
| 2008/0072389 | A1 | 3/2008 | Ghosh | EP | 1 151 728 | 11/2001 |
| | | | | EP | 1 174 055 | 1/2002 |
| | | FOREIGN PATENT DOCUMENTS | | EP | 1 192 933 | 4/2002 |
| | | | | EP | 1 393 711 | 3/2004 |
| CA | | 1082408 | 7/1980 | EP | 1 407 723 | 4/2004 |
| CA | | 1191003 | 7/1985 | EP | 1 415 614 | 5/2004 |
| CA | | 96826 | 7/2002 | EP | 1 457 200 | 9/2004 |
| CN | | 2274947 | 2/1998 | FR | 1357566 | 4/1964 |
| DE | | 1244709 | 7/1967 | FR | 1357570 | 4/1964 |
| DE | | 3328604 | 3/1986 | FR | 1414679 | 10/1965 |
| DE | | 3630153 | 4/1988 | FR | 2368854 | 5/1978 |
| DE | | 3739009 | 6/1989 | FR | 2599961 | 5/1989 |
| DE | | 8900029 | 6/1990 | GB | 1240438 | 7/1971 |
| DE | | 3734860 | 11/1990 | GB | 2005999 | 5/1979 |
| DE | | 3939859 | 6/1991 | GB | 1583558 | 1/1981 |
| DE | | 202004004628 | 8/1991 | GB | 2191016 | 12/1987 |
| DE | | 9215583 | 3/1994 | GB | 2196258 | 4/1988 |
| DE | | 9215595 | 3/1994 | GB | 2228402 | 8/1990 |
| DE | | 29517758 | 4/1996 | GB | 2274061 | 7/1994 |
| DE | | 29505195 | 9/1996 | GB | 2089042 | 3/2001 |
| DE | | 29517610 | 4/1997 | GB | 2097844 | 3/2001 |
| DE | | 19541429 | 5/1997 | GB | 2097845 | 3/2001 |
| DE | | 29621445 | 5/1997 | GB | 2094145 | 5/2001 |
| DE | | 19654108 | 6/1998 | GB | 3008453 | 5/2003 |
| DE | | 19708266 | 9/1998 | GB | 3004567 | 9/2003 |
| DE | | 19824786 | 1/1999 | GB | 3004568 | 9/2003 |
| DE | | 29900775 | 5/1999 | GB | 3014059 | 9/2003 |
| DE | | 29908517 | 1/2000 | GB | 3014060 | 9/2003 |
| DE | | 19950933 | 4/2001 | GB | 3006685 | 10/2003 |
| DE | | 10008753 | 9/2001 | GB | 3006686 | 10/2003 |
| DE | | 10066004 | 12/2001 | GB | 2406503 | 4/2005 |
| DE | | 20013827 | 12/2001 | GB | 2416309 | 1/2006 |
| DE | | 10065705 | 1/2002 | GB | 2416310 | 1/2006 |
| DE | | 10039198 | 2/2002 | GB | 2416311 | 1/2006 |

| | | | | | | |
|---|---|---|---|---|---|---|
| JP | 63-286147 | 11/1988 | | WO | WO 95/22938 | 8/1995 |
| JP | 1-149976 | 6/1989 | | WO | WO 95/26692 | 10/1995 |
| JP | 2-241406 | 9/1990 | | WO | WO 96/03089 | 2/1996 |
| JP | 2-249505 | 10/1990 | | WO | WO 96/09019 | 3/1996 |
| JP | 2-283311 | 11/1990 | | WO | WO 96/10373 | 4/1996 |
| JP | 3-251207 | 11/1991 | | WO | WO 96/36396 | 11/1996 |
| JP | 5-146314 | 6/1993 | | WO | WO 96/38100 | 12/1996 |
| JP | 5-269024 | 10/1993 | | WO | WO 97/01298 | 1/1997 |
| JP | 6-121710 | 5/1994 | | WO | WO 97/16152 | 5/1997 |
| JP | 6-189822 | 7/1994 | | WO | WO 97/21420 | 6/1997 |
| JP | 6-245819 | 9/1994 | | WO | WO 98/06456 | 2/1998 |
| JP | 6-245820 | 9/1994 | | WO | WO 98/10711 | 3/1998 |
| JP | 7-116020 | 5/1995 | | WO | WO 98/18398 | 5/1998 |
| JP | 7-116024 | 5/1995 | | WO | WO 98/18399 | 5/1998 |
| JP | 7-93892 | 10/1995 | | WO | WO 98/23219 | 6/1998 |
| JP | 8-000356 | 1/1996 | | WO | WO 98/27891 | 7/1998 |
| JP | 8-103331 | 4/1996 | | WO | WO 98/30169 | 7/1998 |
| JP | 2-540444 | 4/1997 | | WO | WO 98/30494 | 7/1998 |
| JP | 2-656178 | 5/1997 | | WO | WO 98/32396 | 7/1998 |
| JP | 9-140454 | 6/1997 | | WO | WO 98/58595 | 12/1998 |
| JP | 2-719556 | 11/1997 | | WO | WO 99/07253 | 2/1999 |
| JP | 10-165228 | 6/1998 | | WO | WO 99/07305 | 2/1999 |
| JP | 2-804940 | 7/1998 | | WO | WO 99/10046 | 3/1999 |
| JP | 2-811246 | 8/1998 | | WO | WO 99/10828 | 3/1999 |
| JP | 11-004839 | 1/1999 | | WO | WO 99/12448 | 3/1999 |
| JP | 11-155638 | 6/1999 | | WO | WO 99/15099 | 4/1999 |
| JP | 3-005608 | 11/1999 | | WO | WO 99/37236 | 7/1999 |
| JP | 3-045412 | 3/2000 | | WO | WO 99/43387 | 9/1999 |
| JP | 2000-217844 | 8/2000 | | WO | WO 99/52596 | 10/1999 |
| JP | 2000-344640 | 12/2000 | | WO | WO 99/56810 | 11/1999 |
| JP | 2001-114658 | 4/2001 | | WO | WO 99/59462 | 11/1999 |
| JP | 2001-218624 | 8/2001 | | WO | WO 99/63859 | 12/1999 |
| JP | 2001-299454 | 10/2001 | | WO | WO 99/63900 | 12/1999 |
| JP | 2002-097125 | 4/2002 | | WO | WO 00/07044 | 2/2000 |
| JP | 2002-200101 | 7/2002 | | WO | WO 00/07482 | 2/2000 |
| JP | 2002-306515 | 10/2002 | | WO | WO 00/07514 | 2/2000 |
| JP | 2002-363051 | 12/2002 | | WO | WO 00/07515 | 2/2000 |
| JP | 2003-61986 | * 3/2003 | | WO | WO 00/25665 | 5/2000 |
| JP | 2003-164334 | 6/2003 | | WO | WO 00/37927 | 6/2000 |
| JP | 2003-221321 | 8/2003 | | WO | WO 00/62701 | 10/2000 |
| JP | 2003-221322 | 8/2003 | | WO | WO 01/10327 | 2/2001 |
| JP | 3-458832 | 10/2003 | | WO | WO 01/12181 | 2/2001 |
| JP | 2003-320243 | 11/2003 | | WO | WO 01/26572 | 4/2001 |
| JP | 2004-018444 | 1/2004 | | WO | WO 01/26576 | 4/2001 |
| JP | 2004-105705 | 4/2004 | | WO | WO 01/51005 | 7/2001 |
| JP | 2004-154211 | 6/2004 | | WO | WO 01/62289 | 8/2001 |
| JP | 2004-242841 | 9/2004 | | WO | WO 01/66030 | 9/2001 |
| JP | 2004-323417 | 11/2004 | | WO | WO 01/72301 | 10/2001 |
| JP | 2005-046388 | 2/2005 | | WO | WO 01/76595 | 10/2001 |
| JP | 2005-058594 | 3/2005 | | WO | WO 02/05812 | 1/2002 |
| JP | 2005-081126 | 3/2005 | | WO | WO 02/21970 | 3/2002 |
| JP | 2005-343813 | 12/2005 | | WO | WO 02/22097 | 3/2002 |
| JP | 2006-061292 | 3/2006 | | WO | WO 02/061683 | 8/2002 |
| KR | 125188 | 10/1997 | | WO | WO 02/088290 | 11/2002 |
| RU | 2122337 | 11/1998 | | WO | WO 02/096896 | 12/2002 |
| RU | 2122819 | 12/1998 | | WO | WO 03/007756 | 1/2003 |
| TW | 212909 | 9/1993 | | WO | WO 03/013380 | 2/2003 |
| WO | WO 89/06942 | 8/1989 | | WO | WO 03/013653 | 2/2003 |
| WO | WO 91/06258 | 5/1991 | | WO | WO 03/026528 | 4/2003 |
| WO | WO 91/13570 | 9/1991 | | WO | WO 03/029140 | 4/2003 |
| WO | WO 92/06671 | 4/1992 | | WO | WO 03/039396 | 5/2003 |
| WO | WO 92/13499 | 8/1992 | | WO | WO 03/047454 | 6/2003 |
| WO | WO 92/19178 | 11/1992 | | WO | WO 03/047477 | 6/2003 |
| WO | WO 90/11728 | 4/1993 | | WO | WO 03/059305 | 7/2003 |
| WO | WO 93/15688 | 8/1993 | | WO | WO 03/063722 | 8/2003 |
| WO | WO 93/18715 | 9/1993 | | WO | WO 03/063723 | 8/2003 |
| WO | WO 93/21991 | 11/1993 | | WO | WO 03/076015 | 9/2003 |
| WO | WO 94/01054 | 1/1994 | | WO | WO 03/077996 | 9/2003 |
| WO | WO 94/09718 | 5/1994 | | WO | WO 03/082049 | 10/2003 |
| WO | WO 94/09850 | 5/1994 | | WO | WO 03/082050 | 10/2003 |
| WO | WO 94/22386 | 10/1994 | | WO | WO 03/089063 | 10/2003 |
| WO | WO 95/07731 | 3/1995 | | WO | WO 03/103529 | 12/2003 |
| WO | WO 95/10243 | 4/1995 | | WO | WO 03/103531 | 12/2003 |

| | | |
|---|---|---|
| WO | WO 2004/006065 | 1/2004 |
| WO | WO 2004/012593 | 2/2004 |
| WO | WO 2004/012621 | 2/2004 |
| WO | WO 2004/014181 | 2/2004 |
| WO | WO 2004/014182 | 2/2004 |
| WO | WO 2004/024080 | 3/2004 |
| WO | WO 2004/026075 | 4/2004 |
| WO | WO 2004/026162 | 4/2004 |
| WO | WO 2004/028235 | 4/2004 |
| WO | WO 2004/030891 | 4/2004 |
| WO | WO 2004/033040 | 4/2004 |
| WO | WO 2004/043204 | 5/2004 |
| WO | WO 02/060401 | 6/2004 |
| WO | WO 2004/045538 | 6/2004 |
| WO | WO 2004/049966 | 6/2004 |
| WO | WO 2004/052230 | 6/2004 |
| WO | WO 2004/052407 | 6/2004 |
| WO | WO 02/068576 | 7/2004 |
| WO | WO 2004/069084 | 8/2004 |
| WO | WO 02/087514 | 9/2004 |
| WO | WO 2004/082499 | 9/2004 |
| WO | WO 2004/084752 | 10/2004 |
| WO | WO 2004/087252 | 10/2004 |
| WO | WO 2004/096074 | 11/2004 |
| WO | WO 2004/103171 | 12/2004 |
| WO | WO 2004/103471 | 12/2004 |
| WO | WO 2004/104927 | 12/2004 |
| WO | WO 2004/105874 | 12/2004 |
| WO | WO 2004/108003 | 12/2004 |
| WO | WO 2004/108004 | 12/2004 |
| WO | WO 2004/112535 | 12/2004 |
| WO | WO 2004/112538 | 12/2004 |
| WO | WO 2004/112637 | 12/2004 |
| WO | WO 2005/002458 | 1/2005 |
| WO | WO 2005/004745 | 1/2005 |
| WO | WO 02/067802 | 2/2005 |
| WO | WO 2005/009270 | 2/2005 |
| WO | WO 2005/018475 | 3/2005 |
| WO | WO 2005/023130 | 3/2005 |
| WO | WO 2005/023131 | 3/2005 |
| WO | WO 2005/023143 | 3/2005 |
| WO | WO 2005/023144 | 3/2005 |
| WO | WO 2005/023145 | 3/2005 |
| WO | WO 2005/023146 | 3/2005 |
| WO | WO 2005/025670 | 3/2005 |
| WO | WO 2005/041713 | 5/2005 |
| WO | WO 2005/046793 | 5/2005 |
| WO | WO 2005/065572 | 7/2005 |
| WO | WO 2005/067764 | 7/2005 |
| WO | WO 2005/070129 | 8/2005 |
| WO | WO 2005/072642 | 8/2005 |
| WO | WO 2005/087171 | 9/2005 |
| WO | WO 2005/094719 | 10/2005 |
| WO | WO 2005/099757 | 10/2005 |
| WO | WO 2005/107638 | 11/2005 |
| WO | WO 2005/099513 | 12/2005 |
| WO | WO 2005/120382 | 12/2005 |
| WO | WO 2005/122948 | 12/2005 |
| WO | WO 2005/123023 | 12/2005 |
| WO | WO 2006/003598 | 1/2006 |
| WO | WO 2006/006808 | 1/2006 |
| WO | WO 2006/007136 | 1/2006 |
| WO | WO 2006/012752 | 2/2006 |
| WO | WO 2006/014309 | 2/2006 |
| WO | WO 2006/014363 | 2/2006 |
| WO | WO 2006/014364 | 2/2006 |
| WO | WO 2006/014368 | 2/2006 |
| WO | WO 2006/014369 | 2/2006 |
| WO | WO 2006/014370 | 2/2006 |
| WO | WO 2006/014371 | 2/2006 |
| WO | WO 2006/014402 | 2/2006 |
| WO | WO 2006/014897 | 2/2006 |
| WO | WO 2006/015196 | 2/2006 |
| WO | WO 2006/020698 | 2/2006 |
| WO | WO 2006/026129 | 3/2006 |
| WO | WO 2006/028099 | 3/2006 |
| WO | WO 2006/031242 | 3/2006 |
| WO | WO 2006/034133 | 3/2006 |
| WO | WO 2006/034281 | 3/2006 |
| WO | WO 02/071970 | 4/2006 |
| WO | WO 93/09847 | 4/2006 |
| WO | WO 2006/035443 | 4/2006 |
| WO | WO 2006/035444 | 4/2006 |
| WO | WO 2006/044099 | 4/2006 |
| WO | WO 2006/047868 | 5/2006 |
| WO | WO 2006/050452 | 5/2006 |
| WO | WO 2006/051619 | 5/2006 |
| WO | WO 2006/053207 | 5/2006 |
| WO | WO 2006/055369 | 5/2006 |
| WO | WO 2006/055571 | 5/2006 |
| WO | WO 2006/055572 | 5/2006 |
| WO | WO 2006/055574 | 5/2006 |
| WO | WO 2006/060547 | 6/2006 |
| WO | WO 2006/063131 | 6/2006 |
| WO | WO 2006/063202 | 6/2006 |
| WO | WO 2006/063318 | 6/2006 |
| WO | WO 2006/014365 | 9/2006 |

OTHER PUBLICATIONS

American Opto Plus LED Corp, Part No. L513LBC-15D (spec sheet).
American Opto Plus LED Corp, Part No. L513NBC-15D (spec sheet).
American Opto Plus LED Corp, Part No. L513UBC-S (spec sheet).
International Search Report for Int'l. App. No. PCT/US2004/029334, Sep. 9, 2004.
International Search Report for Int'l. App. No. PCT/US2004/029335, Sep. 9, 2004.
International Search Report for Int'l. App. No. PCT/US2004/029336, Sep. 9, 2004.
International Search Report for Int'l. App. No. PCT/US2004/029337, Sep. 9, 2004.
International Search Report for Int'l. App. No. PCT/US2004/029338, Sep. 9, 2004.
Lumileds Lighting Luxeon Emitter Data Sheet D525.
Marktech Optoelectronics, LC503QBL1-15G (spec sheet).
Marktech Optoelectronics, LC503QBL1-15H (spec sheet).
Nichia, Model NSCx190D (spec sheet).
Opto Diode Corp, OD-470 (spec sheet).
Opto Diode Corp, OD-470L (spec sheet).
Roithner Lasertechnik, EP20-150 Series (spec sheet).
Roithner Lasertechnik, M3L1 Series (spec sheet).
Roithner Lasertechnik, Part No. 5W4HCA-H (spec sheet).
SunLED, T-1 3/4 (5mm) Solid State Lamp (spec sheet) Jul. 6, 2002.
SunLED, XLBB12WH (spec sheet) Sep. 11, 2003.
Super Bright LEDs, Inc. (spec sheet).
Super Bright LEDs, Inc. RL5-B3023 (spec sheet).
Super Bright LEDs, Inc. RL5-B4630 (spec sheet).
Super Bright LEDs, Inc. RL5-B5515 (spec sheet).

* cited by examiner

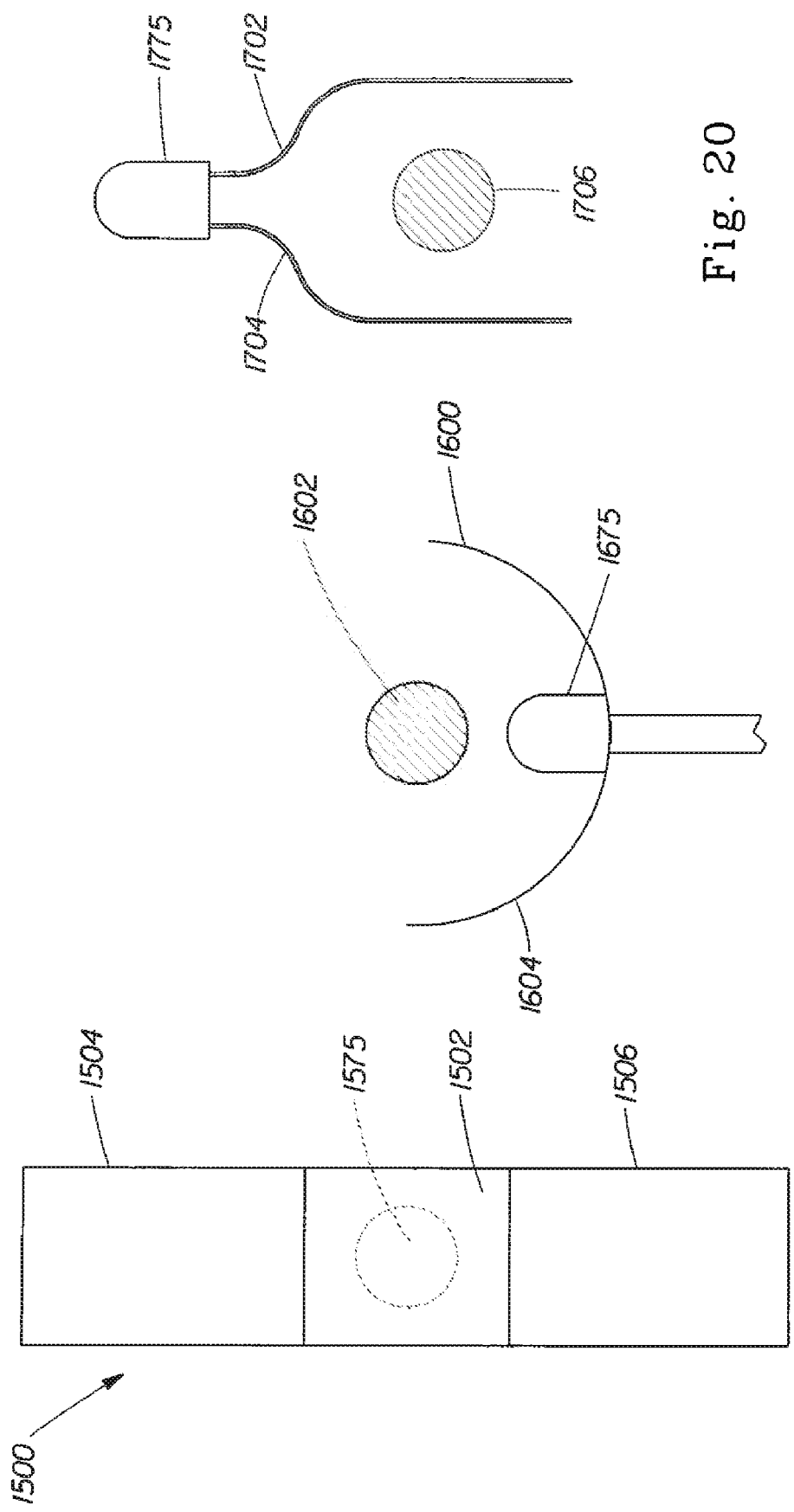

ELECTRIC TOOTHBRUSH COMPRISING AN ELECTRICALLY POWERED ELEMENT

CROSS REFERENCE TO RELATED APPLICATION

This application is a continuation of application Ser. No. 10/888,206 filed on Jul. 9, 2004, now abandoned, which is a continuation in part of application Ser. No. 10/832,168 filed on Apr. 26, 2004, and application Ser. No. 10/842,302 filed on May 10, 2004, now abandoned, and application Ser. No. 10/847,429 filed on May 17, 2004 and application Ser. No. 10/887,644 filed on Jul. 9, 2004 and application Ser. No. 10/887,667 filed Jul. 9, 2004, now abandoned, and claims the benefit of U.S. provisional application Ser. No. 60/501,266 filed on Sep. 9, 2003, all of which are herein incorporated by reference.

FIELD OF THE INVENTION

The present invention relates to electric toothbrushes that utilize a moving bristle holder in conjunction with a light emitting element that illuminates the brushing area and provides a base for the moving bristle holder. In some versions of the toothbrush, a removable head is provided.

BACKGROUND OF THE INVENTION

A toothbrush which emits light or generates other emissions from one or more electrically powered elements disposed on the head of the toothbrush can be provided in a variety of ways. A manual or electric toothbrush can have electrically powered elements disposed in the handle or other area remote from the head, and convey emissions from the electrically powered elements to the head of the toothbrush with transmitters such as fiber optics. However, emissions conveyed through a transmitter such as fiber optics are often diminished. For example, light emitting from a light emitting element that is conveyed via fiber optics can diminish in luminous intensity and/or flux density as it travels the length of the fiber optic transmitter. Alternatively, the electrically powered element can be disposed on the head of the toothbrush. However, an electrically powered element disposed on the head of an electric toothbrush must be of a size and placement such that space remains for bristles and the mechanics of the electric toothbrush. The mechanics of the toothbrush, especially the drive shaft, consume much of the space available within the head and neck of the toothbrush. Additionally, increasing the size of the head and/or handle of the toothbrush to increase space for including the electrically powered element can result in a toothbrush that is too large to effectively and comfortably clean the surfaces of the oral cavity. Therefore, it is desired to have an electric toothbrush wherein an electrically powered element is disposed on the head of the toothbrush such that the mechanics of the toothbrush are not interrupted or otherwise compromised. Further it is desired to have an electrically powered element disposed on the head of the toothbrush such that no fiber optics and/or other transmitters are necessary to convey the emissions from the electrically powered element to the head of the electric toothbrush.

SUMMARY OF THE INVENTION

The present invention provides an electric toothbrush for use in the mouth comprising a handle, a head, and a neck extending between the handle and the head. The handle has a hollow interior region comprising a motor and an electrical power source. The head comprises an ultrasonic transducer and a bristle field. The ultrasonic transducer is in electrical communication with the electrical power source. A shaft is operatively connected to the motor for moving the bristle field.

BRIEF DESCRIPTION OF THE DRAWINGS

The invention may take physical form in certain parts and arrangements of parts, embodiments of which will be described in detail in this specification and illustrated in the accompanying drawings which form a part hereof, and wherein:

FIG. 18 is a partial front elevational view of an embodiment of a drive shaft of a toothbrush made according to the present invention.

FIG. 19 is a cross sectional end view of a drive shaft, a light emitting element, and reflectors of a toothbrush made according to the present invention.

FIG. 20 is a cross sectional end view of a drive shaft and a light emitting element of a toothbrush made according to the present invention.

DETAILED DESCRIPTION OF THE EMBODIMENTS

Figure 1:
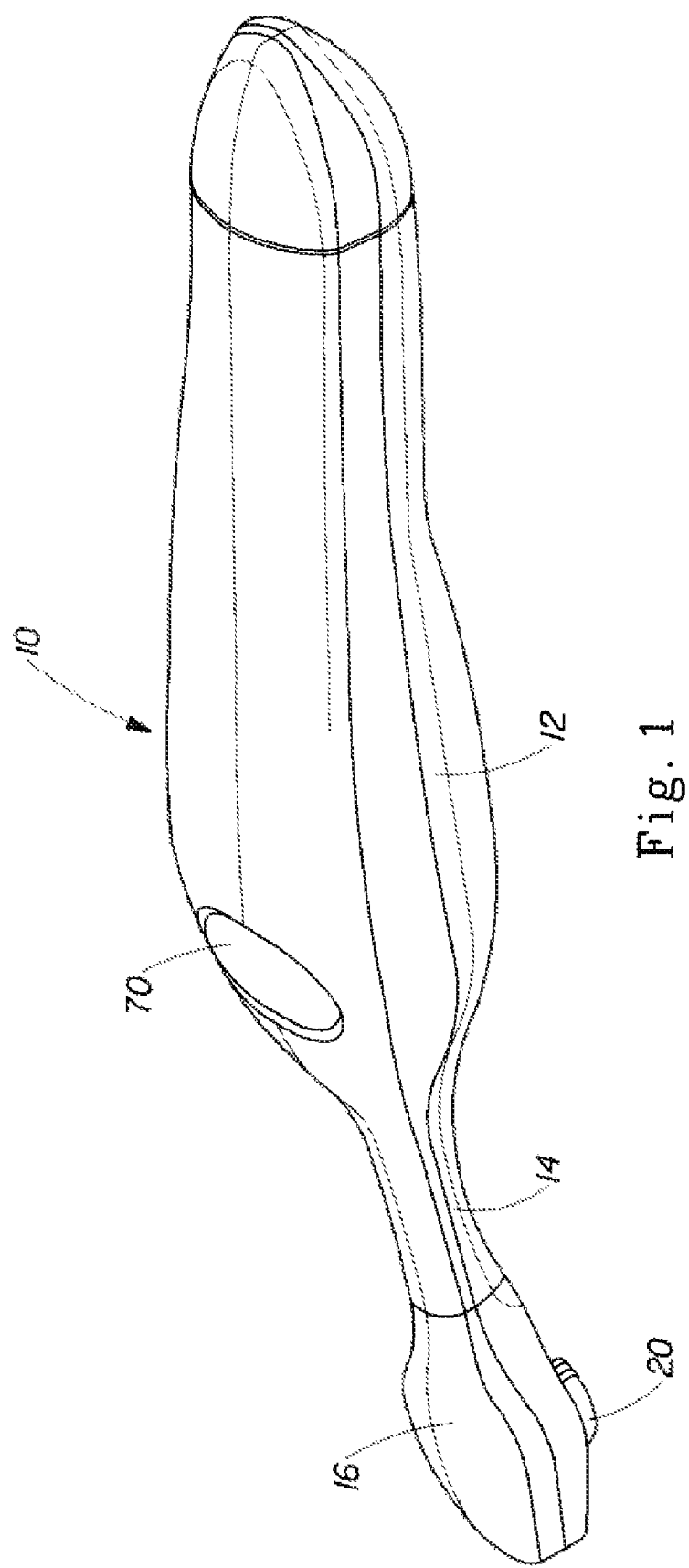
FIG. 1 is a perspective view of an electric toothbrush in accordance with the present invention.

Generally, the present invention relates to an oral care implement for use in the mouth having one or more electrically powered elements disposed on the head including, but not limited to, light emitting diodes, light-emitting elements using incandescent elements, laser elements, halogen elements, neon elements, fluorescent elements, plasma elements, xenon elements, flossing elements, massaging elements, scraping elements, heat emitting elements, sonic wave emitting elements, ultra-sound emitting element, electric current emitting elements, composition emitting elements and/or any combination thereof. Such oral care implements can include, but are not limited to, electric toothbrushes, powered flossers, tooth polishers, gum massagers, etc. As used herein the term electrically powered element includes any electrically powered element that can convert electrical energy at the place where the element is disposed. For example, a light emitting element can convert electrical energy into light at the location where the element is disposed; such as on the head of an electric toothbrush. For simplicity's sake, hereinafter the present invention will be discussed as embodied in an electric toothbrush having a head, on which a light emitting element is disposed. Such electric toothbrushes can be used in personal hygiene to clean one's teeth and gums using a motorized movement, while the electrically powered element is activated. The present invention also relates to an electric toothbrush having a replaceable or removable head and/or neck. Furthermore, the present invention relates to kits including the toothbrush of the present invention.

As used herein, the term "light-emitting" element includes an element that converts electrical energy into light. In one embodiment the light-emitting element of the present invention is a light emitting diode ("LED"). As used herein, the term "light" is intended to encompass the spectrum of both visible and non-visible (e.g., ultraviolet and infra-red) light. The various embodiments of the toothbrushes described herein may utilize light emitting elements having a variety of characteristics. Concerning wave length, the light-emitting elements used in the toothbrushes described herein can emit light having a central wave length between about 10 nm and about $10^6$ nm. In one embodiment of the toothbrush of the present invention the light emitted from the light emitting element can be greater than about 370, 390, 410, 430, 450, 470, 490, 510, 530, 550, 570, 590, 610, 630, 650, 670, 690, 710 nm and/or less than about 770, 750, 730, 710, 690, 670, 650, 630, 610 nm. In another embodiment the light emitted can have a wavelength of greater than about 420, 430, 440, 450, 460, 470, 480, and/or 490 nm and/or less than about 490, 480, 470, 460, 450, 440, 430, 420 nm. It will be appreciated that the particular range of wavelengths selected can depend upon the desired color of the light. In one embodiment the light emitted can be a blue color.

In one embodiment, the electric toothbrush includes an elongated body portion or handle, a head, and a neck extending between the head and the handle. One or more light-emitting elements can be provided on the head, adjacent to, on, or in one or more static or moving bristle holders having a plurality of bristles thereon. Incorporating a light emitting element into the head of an electric toothbrush can result in interference with the mechanics of the electric toothbrush, particularly the operative connection between the drive shaft and the movable bristle holder(s), depending on where the light emitting element is disposed. To prevent such interference the one or more light-emitting elements can be positioned such that the light emitting element is not disposed between the motor and the movable bristle holder. In certain embodiments, a light-emitting element can be positioned at the center or at the axis of movement of an oscillating bristle holder. Additionally, the light emitting element can act as the pin which serves as the contact surface and/or center or axis of rotation for a movable bristle holder. When the light emitting element is positioned within the movable bristle holder, particularly as the axis and/or center of rotation, the light emitting element is not disposed between the motor and the movable bristle holder, therefore the drive shaft can operatively connect with the movable bristle holder without interference from the light emitting element. Additionally, the light emitting element can refine the movement of the movable bristle holder, preventing the movable bristle holder from undergoing undesirable movement. For example, the light emitting element serving as a pin in the center of an oscillating movable bristle holder can prevent non-rotational or non-oscillating movement of the oscillating bristle holder. The light-emitting element can be stationary, or it can be secured to the movable bristle holder so that the element moves with the bristle holder. In other embodiments the light emitting element is disposed on the distal end of the toothbrush head, distal to the movable bristle holder. This embodiment also avoids interference with the operative connection between the movable bristle holder and the drive shaft.

In other embodiments wherein the light emitting element is disposed between the motor and the movable bristle holder, the operative connection between the drive shaft and the movable bristle holder can be achieved with a drive shaft that bypasses the light emitting element, a drive shaft that serves as a base or support for the light emitting element, a drive shaft that passes over the light emitting element wherein at least a portion of the drive shaft is transparent to the emitted light, a drive shaft that passes underneath a light emitting element, and/or modifying a light emitting element such that the drive shaft becomes a part of the light emitting element. The bristle holder can, in certain embodiments, feature a region, typically provided at the center of the holder, which promotes the passage of light there through. That region may be formed from a transparent or translucent material, or alternatively, the region can be an aperture or other open area substantially free of bristles thereby permitting the passage of light. This region can be provided at any portion of the head of the toothbrush, including the center of a movable bristle holder. Alternatively, the electric toothbrush may have a light emitting element disposed on one portion of the head of the toothbrush, and a different electrically powered element, such as an ultra-sound emitting element, disposed on another portion of the head of the toothbrush.

The head includes a longitudinal axis, one or more moving bristle holders or carriers and, optionally, one or more static or fixed bristle holders. The moving bristle holders may rotate, swivel, gyrate, oscillate, linearly reciprocate, or undergo any combination of motions. The type of motion provided by the electric toothbrushes of the present invention can be widely varied. The static bristle holders and the arrangement of the static bristles disposed thereon can also be widely varied. For example, the static bristles might partially or wholly circumscribe the moving bristle holders or may be disposed in a gap between the moving bristle holders. Examples of some bristle holder motions and bristle arrangements suitable for use with the present invention are described in US 20030126699; US 20030084525; US 20030084524; US 20030084526; and WO 03/063723; and WO 03/063722. The bristles can be made from conventional non-elastomeric materials, such as polyethylene, or can be made from elastomeric materials such as natural or synthetic rubbers, polyolefins, polyetheramides, polyesters, styrenic polymers, polyurethanes, etc., or a combination of materials.

The handle has a hollow portion with a motor disposed therein that is operably connected to the moving bristle holders. A shaft extends from the motor through the neck and into at least a portion of the head. The shaft may rotate, oscillate, linearly reciprocate, gyrate, orbit, or move in a conical fashion when driven by the motor in order to impart one or more motions to the moving bristle holders. A gearing arrangement can be provided between the motor and the shaft or between the shaft and the moving bristle holders in order to impart motion thereto. Exemplary shaft and/or gearing arrangements are shown in U.S. Pat. Nos. 6,360,395 and 5,617,601, and U.S. Patent Application Nos. 2003/0134567 and 2003/0163881 as well as in other patents and patent publications referenced herein. The handle also has a power source, such as one or more batteries, disposed therein for powering the motor and the light-emitting elements. Alternatively, the electric toothbrush may be connected to an external power source for powering the motor. A switch is disposed on the handle for activating the motor and/or light-emitting elements. The switch includes an actuator button and a metal contact. The switch is manually depressed by pressing a molded actuator button down, which presses against a metal contact, completing the circuit, as in a conventional momentary switch. The switch allows continuous operation, through a ramp design, by depressing and sliding the actuator button forward as in a conventional continuous switch. By combining these two functions in one switch, the consumer can try the unit and see its operation prior to purchase, and still operate it continuously once out of the package. The switch can also activate one or more light emitting elements. The light emitting elements are energized whenever the motor is activated, however, the electric toothbrush can also have a switch designated to activate the light emitting element.

Referring now to the drawings which illustrate the embodiments of the invention only and not for purposes of limiting same, FIG. 1 shows an electric toothbrush 10 according to an embodiment of the present invention. The electric toothbrush can be used for personal hygiene such as brushing one's teeth and gums. As shown in FIG. 1, the electric toothbrush includes a handle 12 and a neck 14 attached to the handle 12. A head 16 is attached to the neck 14. Typically, the head is larger than the neck 14, which is also typically smaller than the handle 12.

Figure 2:
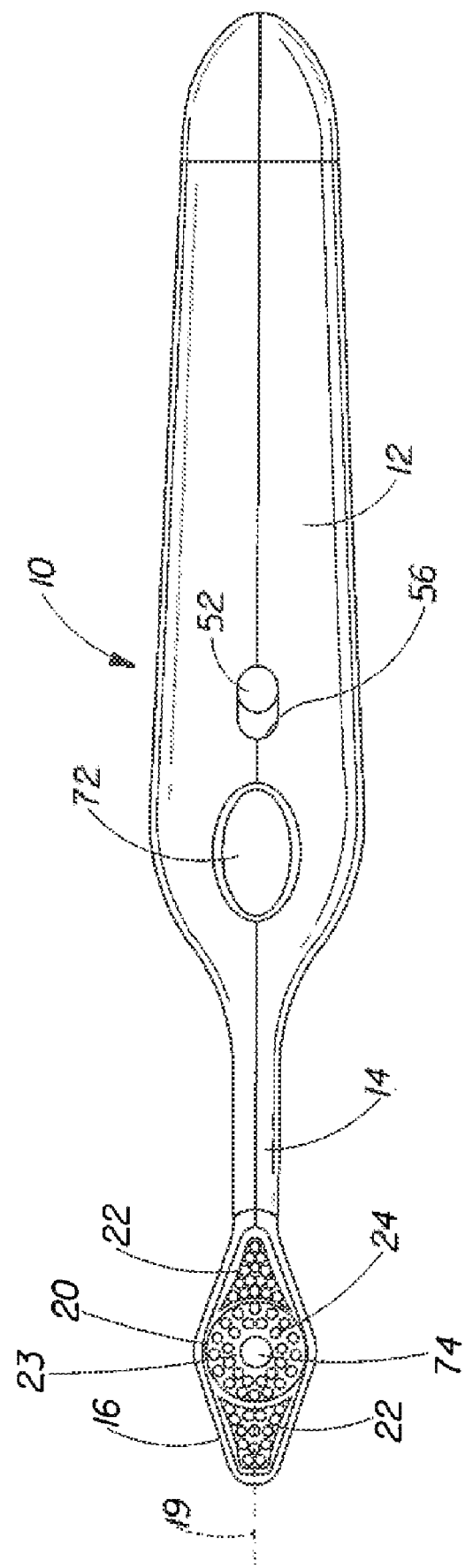
FIG. 2 is a top planar view of the electric toothbrush of FIG. 1.
Figure 2A:
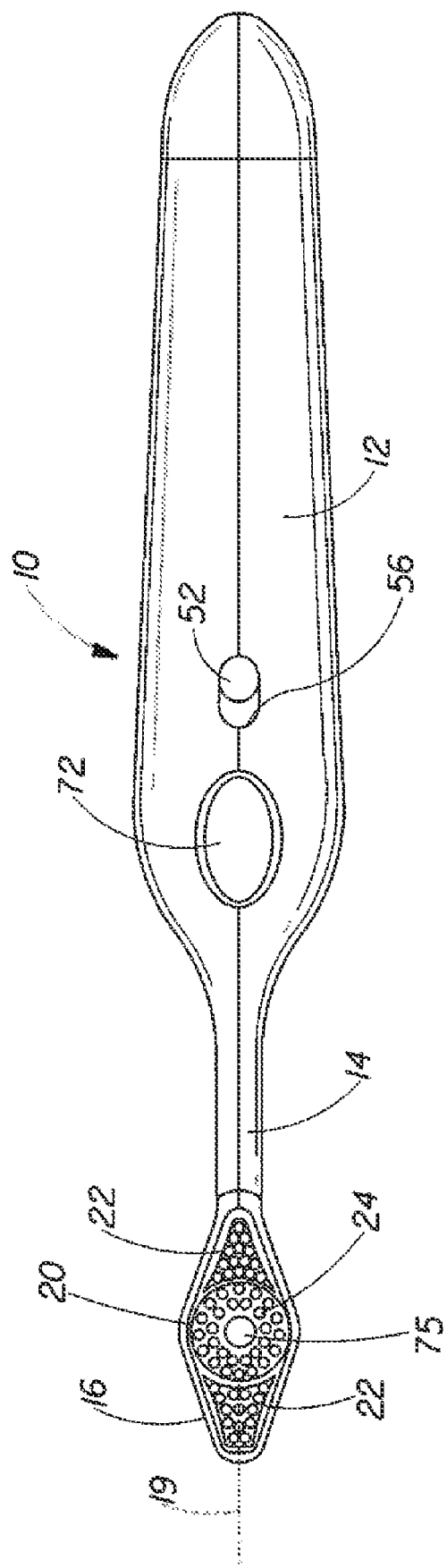
FIG. 2a is a top planar view of the electric toothbrush of FIG. 1.
Figure 22:
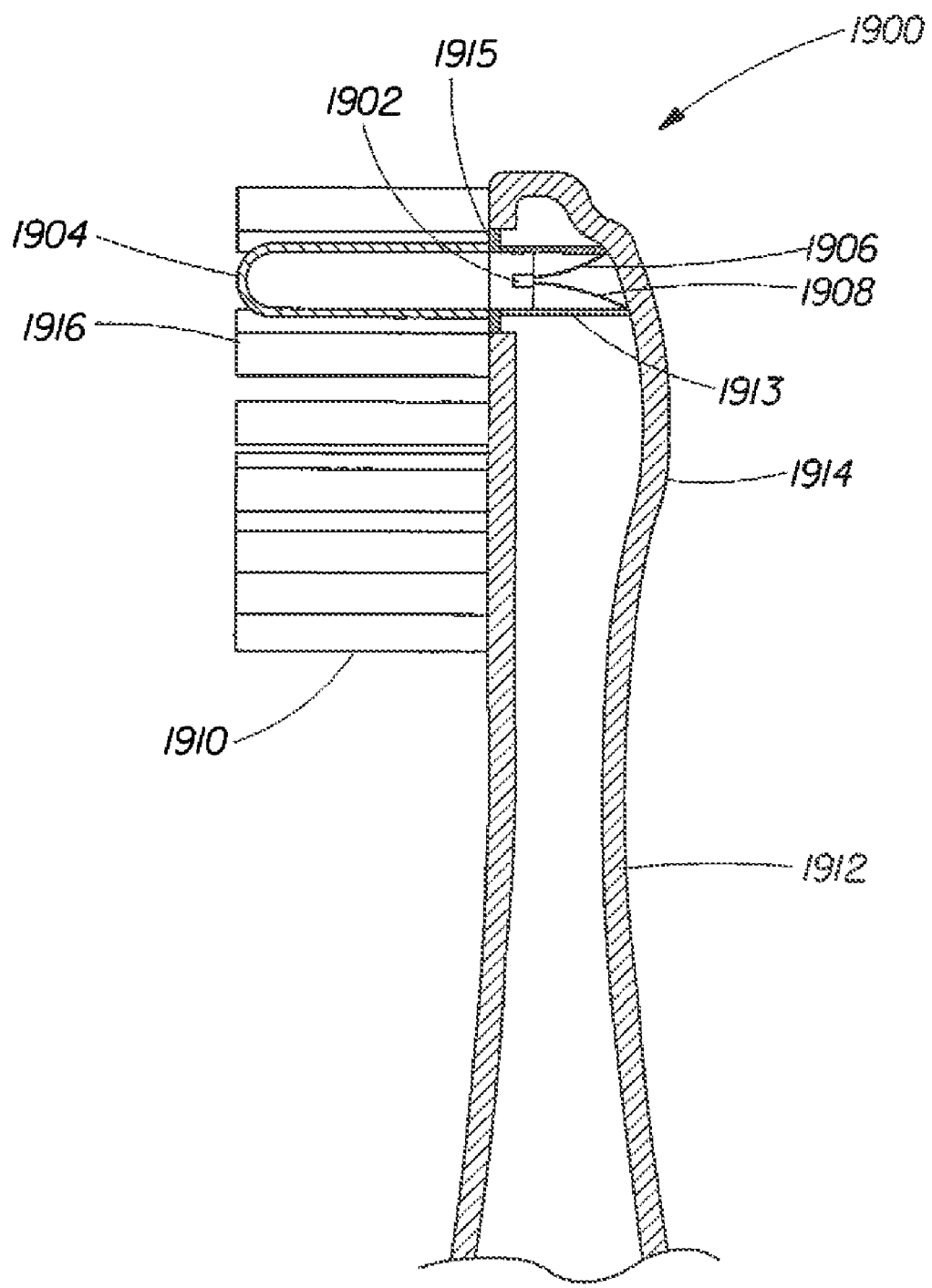
FIG. 22 is a cross-sectional side elevational view of an embodiment of the electric toothbrush of the present invention.

Referring now to FIG. 2, the head 16 further is defined by a longitudinal axis 19, and comprises a moving bristle holder 20 and one or more optional static bristle holders 22. In this embodiment the static bristle holders 22 are located on opposite sides of the moving bristle holder 20. The moving bristle holder 20 in this embodiment is located at the center of the head 16. The moving bristle holder 20 includes a plurality of bristles 24 supported and retained on the holder 20. The moving bristle holder can oscillate or rotate about an axis of motion approximately normal to the longitudinal axis 19 of the head 16, although other motions may be provided as previously described. As described in greater detail herein, disposed along this axis of motion of the moving bristle holder, is an electrically powered element 74. In a particular embodiment (as shown in FIG. 2*a*), the electrically powered element is a light-emitting element 75 such as a light emitting diode positioned on the head of the toothbrush and generally below or under where the surface of the light emitting element does not extend beyond the bristle bearing surface of the moving bristle holder (as shown in FIG. 22). In certain configurations, the moving bristle holder rotates on, pivots on, or otherwise undergoes motion with respect to the light-emitting element which can be stationary. Ideally in this configuration, the light-emitting element 75 can serve as a base, thereby serving as a supporting contact surface for the moving bristle holder 20. The noted axis of motion can extend through, and depending upon the shape and orientation of the light-emitting element, be colinear therewith.

Figure 3:
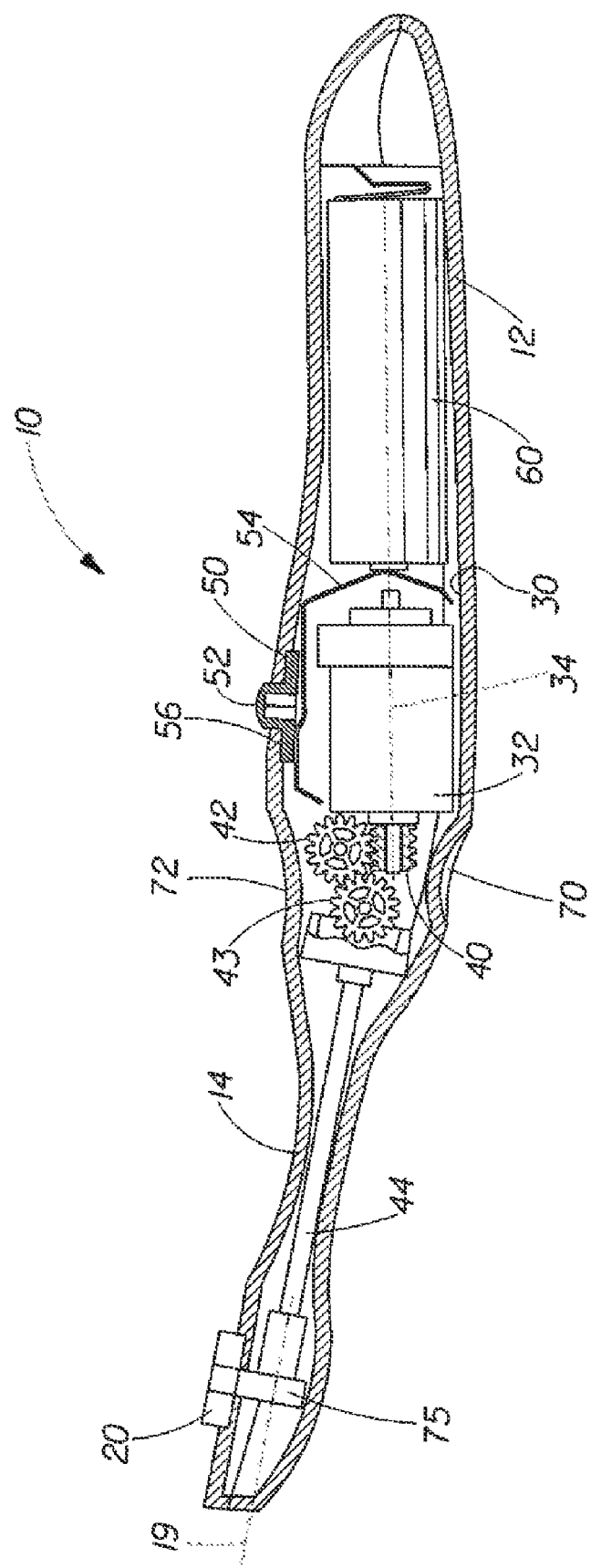
FIG. 3 is a cross-sectional side elevational view of the electric toothbrush of FIG. 1.

As shown in FIG. 3, the handle 12 further includes a hollow interior region 30 which houses a motor 32. The hollow interior region 30 generally extends along an axis 34 and retains the motor 32 and one or more electrical power sources such as a battery 60. Switching elements or contacts 50 and 54 can be utilized in conjunction with the switch 52 to selectively operate the motor 32 and the light emitting element 75. In this embodiment the motor 32 powers the moving bristle holder 20 through a rotatable shaft 44. The shaft 44 rotates or oscillates about an axis 19. A gearing arrangement is operatively interconnected between the shaft 44 and the motor 32. The gearing arrangement includes a worm gear 40 and a pair of step gears 42, 43. The motor 32 is operatively connected to the worm gear 40. Step gear 42 is operatively connected to step gear 43 and the worm gear 40. The light emitting element 75 is disposed in the interior of the toothbrush head. A switch 52 is provided to control operation of the electric toothbrush and is operatively connected to the motor 32. The switch 52 is also configured to operate the one or more light emitting elements of the toothbrush. Such can be momentary or continuous. When the switch 52 is closed, a circuit is completed between the battery 60 provided within the hollow interior region 30 of the handle 12 and the motor 32 and light emitting element 75.

Figure 3A:
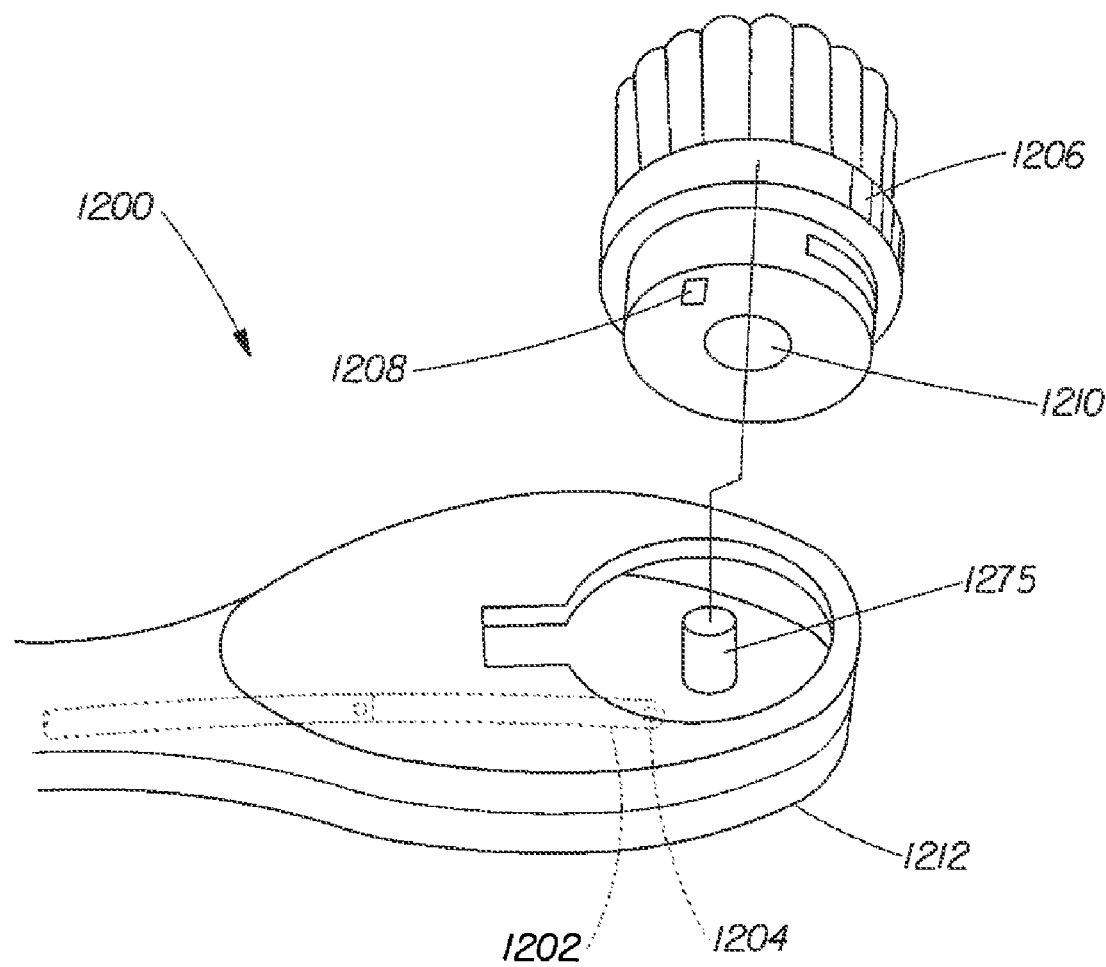
FIG. 3a is a cross-sectional side elevational view of the head portion of an embodiment of the present invention.
Figure 3B:
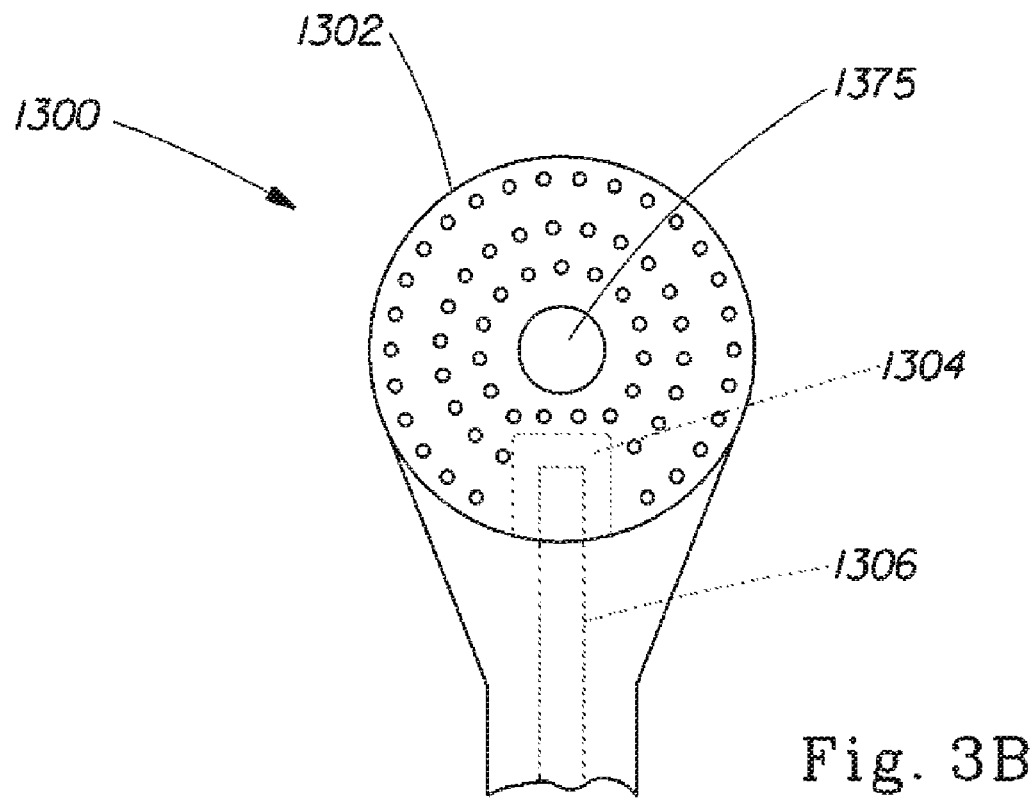
FIG. 3b is a partial front view elevational view of a head and neck of an embodiment of the present invention.
Figure 3C:
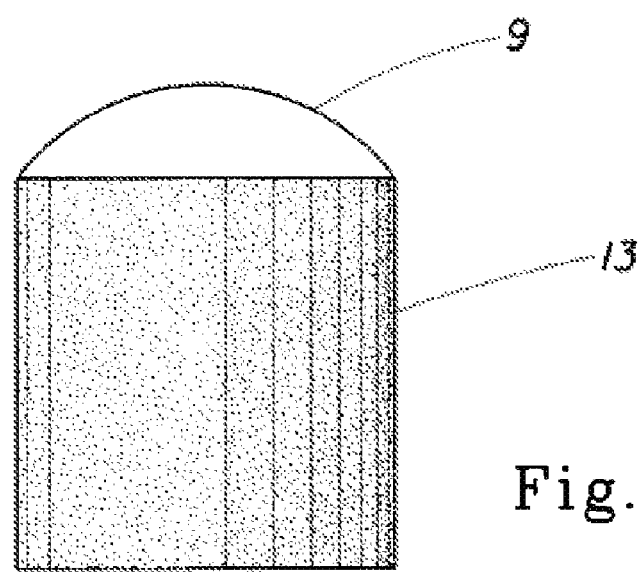
FIG. 3c is a partial front view of the lens of a light emitting element.

FIG. 3a-3b illustrate embodiments of the electric toothbrush wherein at least a portion of the light emitting element is the pin and/or contacting surface which serves as the axis or center of rotation for a movable bristle holder. To protect the light emitting element from damage resulting from contact with the movable bristle holder, the light emitting element can be disposed within a protective pillar, the outer surfaces of the light emitting element or the lens of the light emitting element can be coated with a protective material. The coating on the outer surfaces can be layered, and can comprise a variety of materials. These materials can include polymers, metals and/or any other material which reinforces and/or strengthens the surfaces of the light emitting element. Additionally, to facilitate smooth movement of the movable bristle holder around the light emitting element, the light emitting element can be coated with a friction reducing material. If the lens serves as the pin for the movable bristle holder, the lower portion of the lens 13 can be opaque and not transparent and/or translucent, and the upper portion of the lens 9 can be transparent and/or translucent, such that light emits from the upper portion of the lens as shown in FIG. 3c.

In one embodiment of the toothbrush head 1200 illustrated in FIG. 3a the drive shaft 1202 comprises an aperture 1204, and the movable bristle holder 1206 comprises a protuberance 1208. Protuberance 1208 fits into aperture 1204, thereby operatively connecting the drive shaft 1202 to the movable bristle holder 1206. The movable bristle holder 1206 also comprises an aperture 1210. The light emitting element 1275 fits into aperture 1210 when the movable bristle holder is secured to the head 1212 of the toothbrush. Upon operation of the toothbrush, the motion of the drive shaft 1202 is translated to the movable bristle holder 1206, which oscillates about the light emitting element 1275. In this embodiment the drive shaft reciprocates.

In the embodiment of the toothbrush head 1300 illustrated in FIG. 3b, the movable bristle holder 1302 comprises an aperture 1304 and the drive shaft 1306 fits into aperture 1304, thereby operatively connecting drive shaft 1306 and the movable bristle holder 1302. When the electric toothbrush is operated the motion of the drive shaft 1306 is translated to the movable bristle holder 1302, which oscillates about the light emitting element 1375. In this embodiment of the toothbrush, the drive shaft has a conical driving motion.

Figure 4:
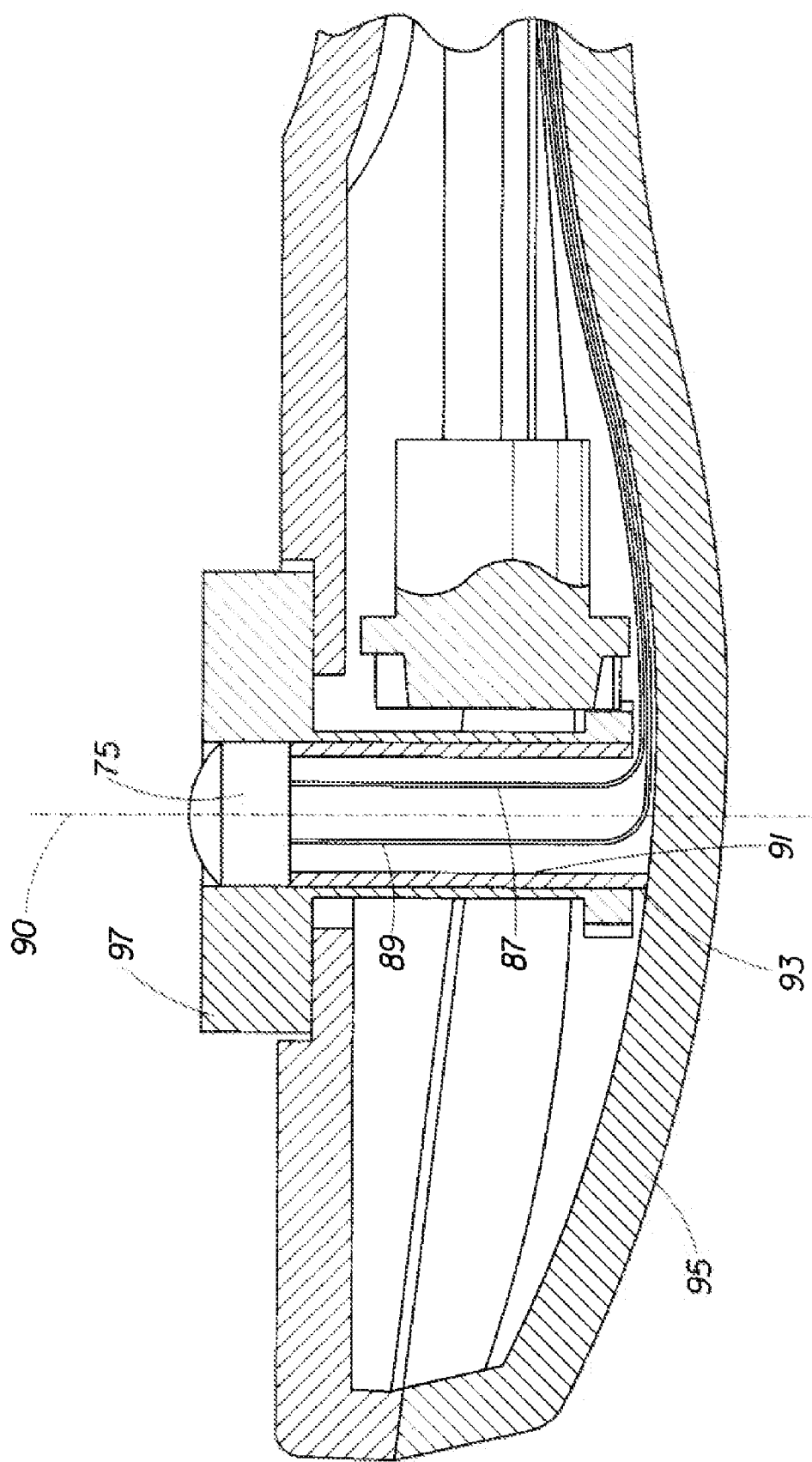
FIG. 4 is a detailed cross-sectional side elevational view of the head of the electric toothbrush according to the present invention.

FIG. 4 illustrates an embodiment of the toothbrush having a stationary light emitting element 75 that is connected to and/or disposed within a pillar 91 that is stationary and fixed to the head 95 at point 93 of the toothbrush. In this embodiment the moving bristle holder 97 oscillates or rotates around the stationary light emitting element 75 disposed within pillar 91. This light emitting element 75 disposed within the pillar 91 serves as the axis of rotation for the moving bristle holder 97 on the head 95 of the toothbrush. The positive lead 87 and the negative lead 89 can run from the light emitting element 75 through the pillar 91 and then down the length of the head 95 and neck (not shown) of the toothbrush to the power source (not shown).

Figure 5:
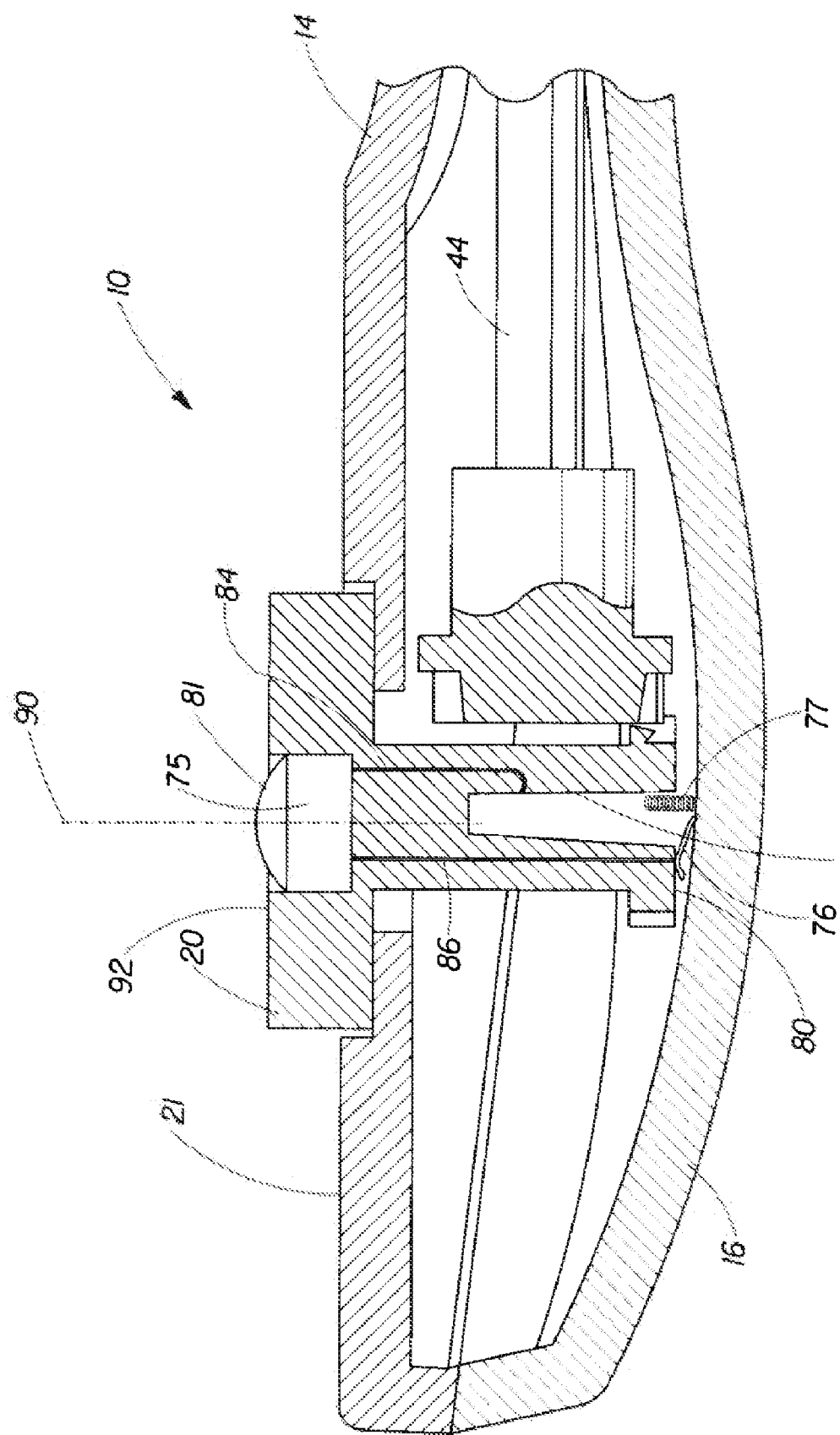
FIG. 5 is a detailed cross-sectional side elevational view of the head of the electric toothbrush of FIG. 1.

Referring to FIG. 5, in this embodiment the electric power is provided to the light-emitting element 75 by the use of a pair of electrical contacts 76 and 77 that slidingly contact dedicated contact regions defined along the underside of the moving bristle holder 20, as shown by way of example in FIG. 4. Electrical wires (not shown) may be provided from the switch and power source to the contacts 76 and 77 for conducting electricity from the power source to the light-emitting element. The wires may run from the handle through the neck 14 to the head 16. The wires can be disposed adjacent the interior wall of the neck 14 so that they do not interfere with the movement of the shaft 44. Alternatively, the wires may be embedded within the neck 14.

It is contemplated that circular electrically conductive contact regions 80 and 82 could be provided along the exterior of the moving bristle holder 20, which regions would be in electrical communication with the pair of fixed contacts 76 and 77 provided within the interior of the head. The electrically conductive contact regions 80 and 82 are insulated from each other by a non-conductive material. Electrical leads 84 and 86 can be provided from the electrically conductive contact regions to the light-emitting element. FIG. 5 illustrates the light-emitting element 75 disposed in contact with or within the moving bristle holder 20. In this embodiment the light-emitting element is fixedly attached to the moving bristle holder 20 and therefore moves with the bristle holder. As shown, the bristle holder 20 and light emitting element 75 oscillate about an axis 90. In one embodiment the top surface such as lens 81 of the light-emitting element is flush with the top surface 92 of the moving bristle holder 20, although the top surface may extend above the top surface 92 if desired. Bristles (not shown) can be disposed on the top surface 92. Additional light-emitting elements can be provided in or on the static bristle holders 22 (FIG. 2).

FIGS. 1-5 collectively illustrate other features of the toothbrush embodiment 10. For example, the toothbrush may feature one or more gripping regions such as 70 and 72; and, as previously noted, the switch 52 that may be selectively positioned within a switching region 56 defined along the handle 12. Upon activation, the light emitting element illuminates the region and specifically, the brushing environment, to which a face surface 21 of the head 16 is directed.

Figures 6, 6A:
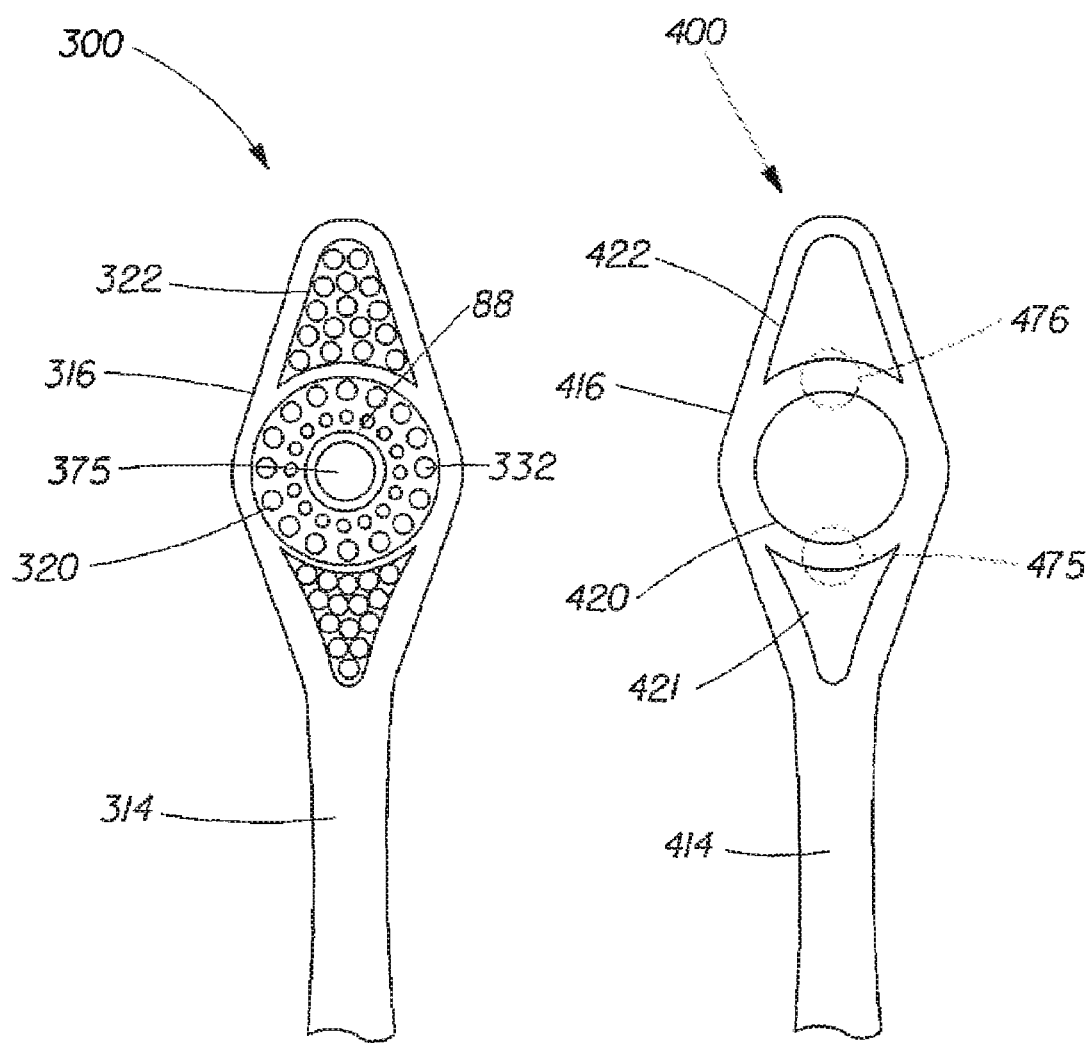
FIG. 6 is a partial front elevational view of a head and neck of another embodiment of the present invention.
FIG. 6a is a partial front elevational view of a head and neck of another embodiment of the present invention.

In another, related embodiment 300, the light-emitting element 375 is disposed within an aperture or hole 88 that extends through a moving bristle holder 320, as best seen in FIG. 6, so that the light-emitting element is stationary and the moving bristle holder 320 oscillates or rotates about the stationary light-emitting element 375. FIG. 6 depicts a toothbrush embodiment 300 having a head 316 and a neck 314 with the movable bristle holder 320 disposed on the head. A plurality of bristles 332 are supported on the holder 320. The head may include a region of static bristles 322. In this embodiment, the light-emitting element 375 is fixedly secured to the head 316. The light-emitting element 375 might extend partially through the hole 88 or it may be disposed below the lower surface of the moving bristle holder 320 so that it is completely contained within the head 316. The centerline or axis of the light-emitting element 375 may also be the axis of rotation or oscillation for the moving bristle holder 320. In some of the above-described embodiments, particularly where the light-emitting element is disposed below the movable bristle holder 320, the moving bristle holder can be formed from a transparent or translucent material. This characteristic promotes the transmission of light from the one or more light-emitting elements to the brushing region. This configuration can protect the light-emitting element from saliva, water, and oral compositions used with the electric toothbrush. It is also contemplated that the bristle holder may be formed from a colored or tinted material.

A variety of materials may be used for forming a transparent or translucent bristle holder and/or head. Examples of such materials include, but are not limited to, polystyrene (PS), polycarbonate (PC), polymethyl methacrylate (PMMA), polyethylene terephthalate glycol (PETG) (commercially available under the designation Eastoman BR003), cellulose acetate propylate (CAP), and combinations thereof. It is contemplated that one or more thermal treatments may be employed to facilitate processing of these materials.

In each of the above-described embodiments, the light-emitting element is disposed in, on, below or directly adjacent the moving and/or static bristle holders so that the light is directed onto the brushing area as efficiently as possible. Further, the light-emitting elements can be arranged so that the principal direction of light emission is generally perpendicular to the top surface of the bristle holders i.e. generally parallel to the direction of the bristles of the bristle holder. In one embodiment, the light-emitting element can be arranged so that the centerline or axis of movement 90 of the light-emitting element is generally perpendicular to the top surface of the head and/or bristle holder, as best seen in FIG. 4. The centerline 90 typically passes through the lens 81 or aperture of the light-emitting element 75. When the light-emitting element is disposed within, on, or below a moving and/or static bristle holder, a cylindrical region comprising the light emitting element, or volume about the centerline 90 of the light-emitting element can be devoid of bristles so that light is transmitted to the brushing surface without interference from the bristles. The diameter of the cylindrical region that is devoid of bristles can be greater than about 2, 4, 6, 8, 10, 12, 14, 16, 18, 20 mm and less than about 20, 18, 16, 15, 14, 12, 10, 8, 6, 4, 2 mm. The moving bristle holder still, however, can have at least one ring of bristles that encircle the light-emitting element, as shown by way of example in FIG. 6. Additional bristle tufts or an inner ring of bristle tufts can also be provided.

Figures 7, 7A:
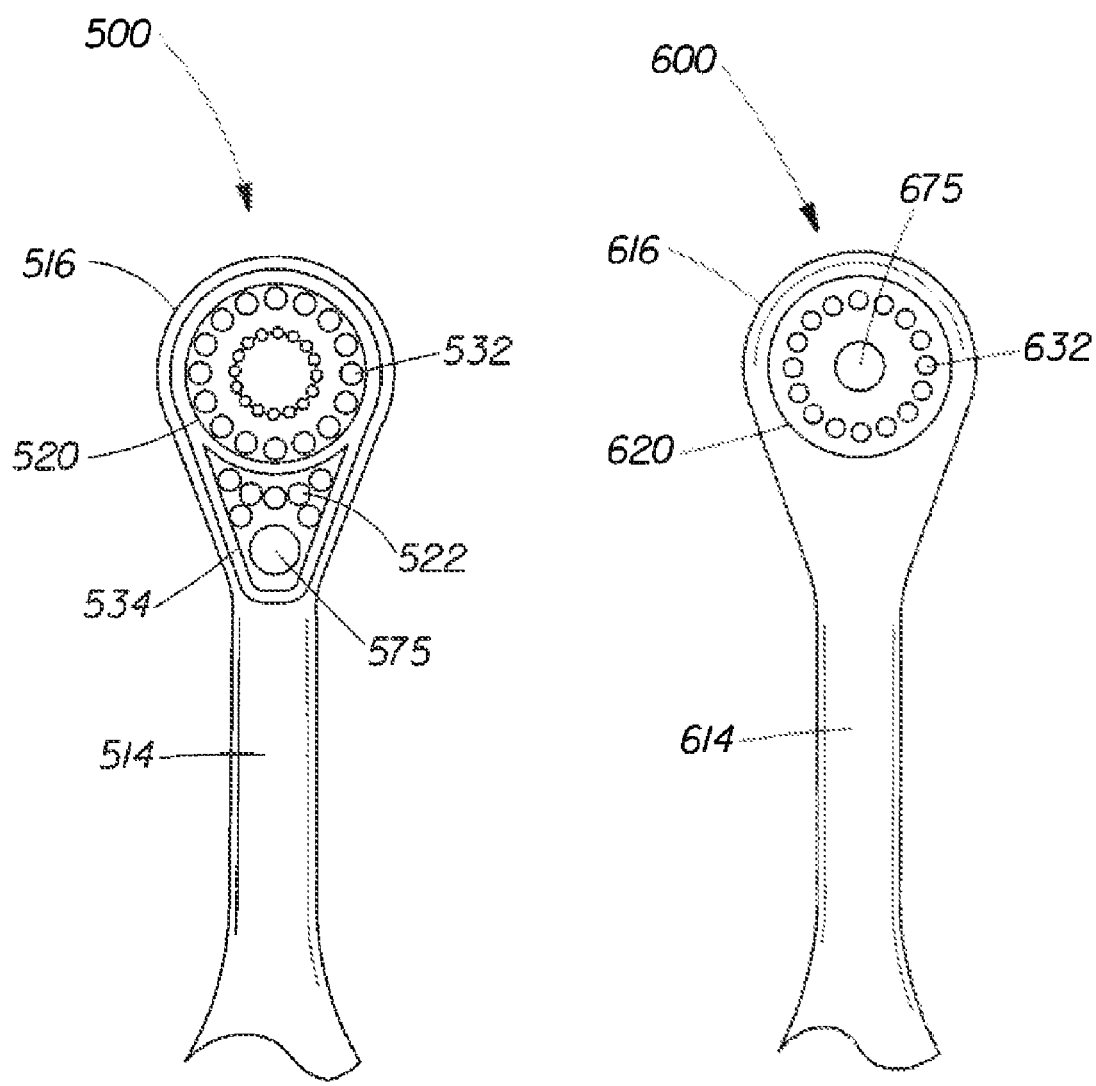
FIG. 7 is a partial front elevational view of a head and neck of yet another embodiment of the present invention.
FIG. 7a is a partial front elevational view of a head and neck of yet another embodiment of the present invention.
Figure 8:
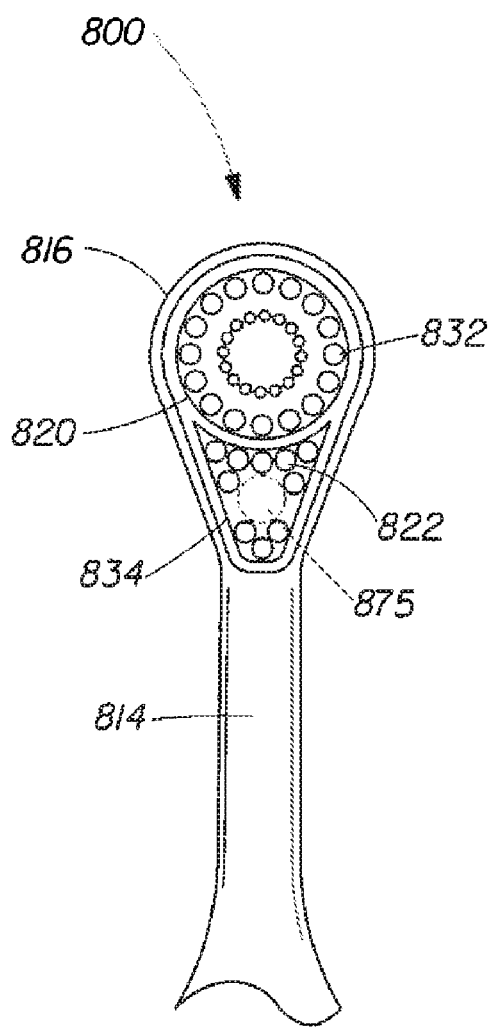
FIG. 8 is a partial front elevational view of a head and neck of still another embodiment of the present invention.

FIGS. 7a and 8 illustrate toothbrush heads, bristle holders and bristle configurations for embodiments of the electric toothbrush made according to the present invention, all of which contain one or more light emitting elements.

FIG. 7a depicts a toothbrush embodiment 600 having a head 616 and a neck 614 in accordance with the present invention. The head 616 comprises a single bristle holder 620 having light-emitting element 675 disposed therein. The bristle holder 620 includes one or more rings of concentric circles of bristles or bristle tufts 632.

Figure 8A:
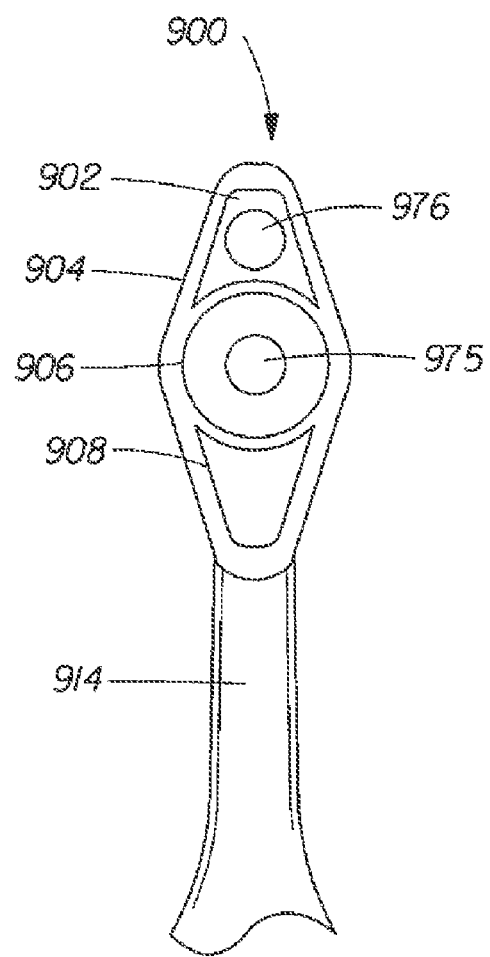
FIG. 8a is a partial front elevational view of a head and neck of still another embodiment of the present invention.

FIG. 8 depicts another toothbrush 800 having a head 816 and a neck 814. The head 816 has a first bristle holder 820 that moves and a second bristle holder 822 that is fixed or stationary. Both bristle holders have light-emitting elements 875 disposed thereon. The first bristle holder 820 has a plurality of bristle tufts 832 that encircle the light-emitting element 875 disposed thereon, and the second bristle holder 822 has a plurality of bristle tufts 834 that surround the light-emitting element 875 disposed thereon. FIG. 8a depicts another embodiment of the present invention. The head and neck of toothbrush 900 comprises three bristle holders 902, 906, and 908, and two light emitting elements 975 and 976. Light emitting element 976 is disposed on bristle holder 902 located at the distal end of the head 904 of the toothbrush 900. Light emitting element 975 is disposed on the movable bristle holder 906 disposed in the center of the head of the toothbrush 900. Finally bristle holder 908 is disposed on the head of the toothbrush proximal to the handle 914. Bristle holders 902 and/or 908 can be either movable or stationary.

Figure 9:
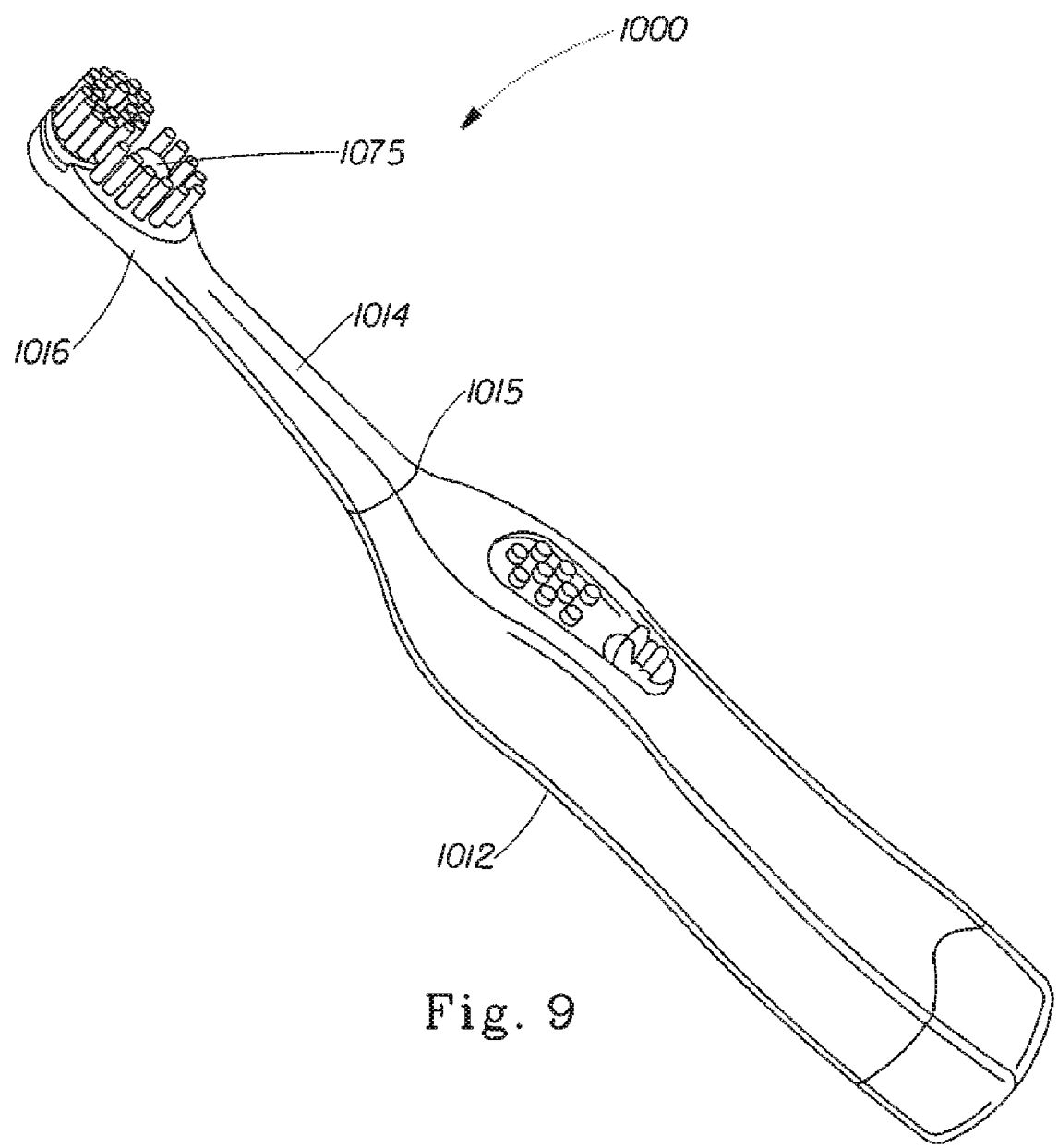
FIG. 9 is a perspective view of another embodiment of the electric toothbrush of the present invention in which the toothbrush includes a head and neck that can be separated from the handle.

As shown in FIG. 9, another electric toothbrush 1000 is depicted having a head 1016, a neck 1014, and a handle 1012. Disposed on the head 1016 is a light-emitting element 1075. The neck and handle are replaceable, and are releasably connected at 1015 and contain corresponding structures for their physical engagement and for establishing electrical communication between the light-emitting element and the power source.

FIGS. 10-13 illustrate another embodiment of the present invention toothbrushes. Toothbrush 1100 comprises a head 1116 and a handle or body (not shown), and a neck 1114 extending between the head and handle. Although this particular embodiment is shown and described as having a removable head and neck, in no way is the present invention limited to this configuration. Disposed on the head 1116 is a first movable bristle holder 1120 and an optional second bristle holder 1122. The second bristle holder 1122 can be movable. However, it is also contemplated that the second bristle holder is stationary. Each of the bristle holders defines a plurality of apertures or recessed regions adapted for retaining tufts of bristles. For example, the first bristle holder 1120 defines a plurality of recesses or apertures for receiving bristles 1124. And, the optional second bristle holder 1122 defines a plurality of recesses or apertures adapted for retaining a plurality of bristles 1126. It will be appreciated that the toothbrush 1100 may utilize one or more arrays of fixed or stationary bristles instead of, or in addition to, the first bristle holder 1120 and associated bristles 1124, and the second bristle holder 1122 and associated bristles 1126.

Figure 11A:
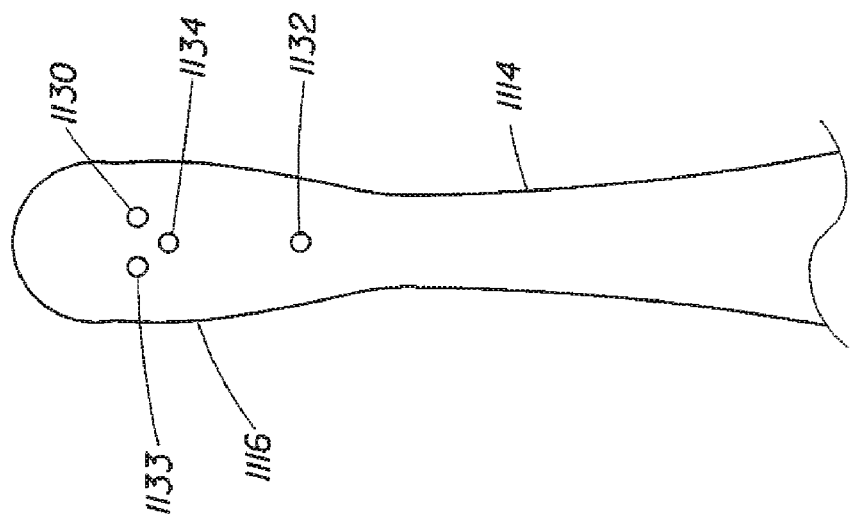
FIG. 11a is a back elevational view of the head and neck of the embodiment illustrated in FIG. 10.
Figure 11:
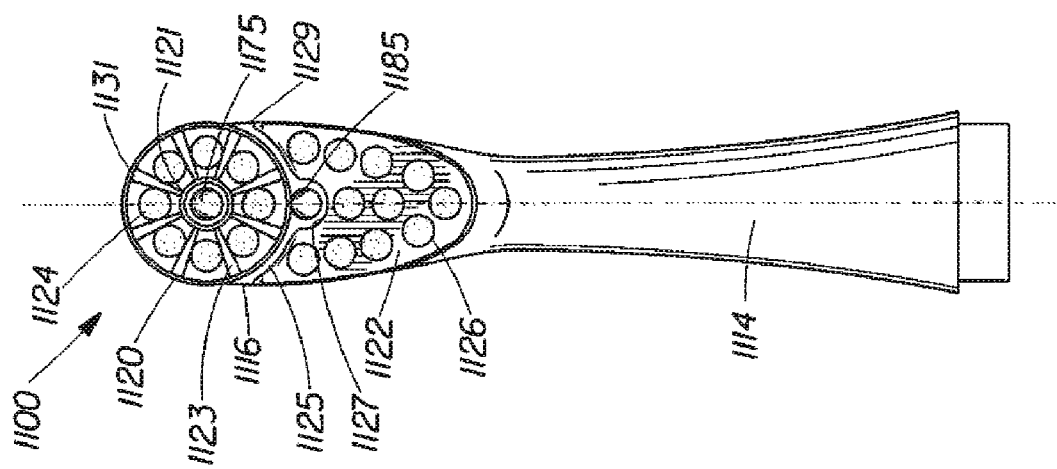
FIG. 11 is a front elevational view of the head and neck of the embodiment illustrated in FIG. 10.
Figure 12:
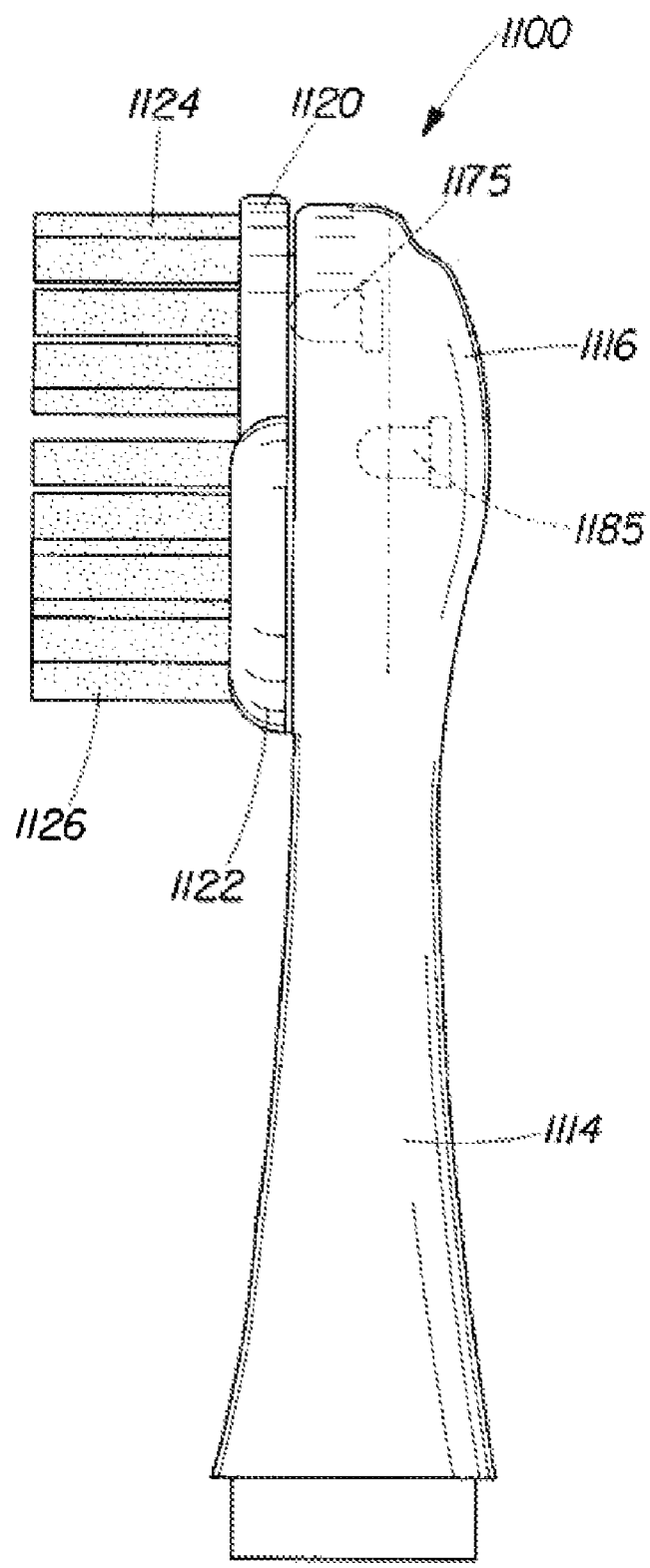
FIG. 12 is a side elevational view of the head and neck of the embodiment shown in FIG. 10.

The toothbrush 1100 comprises one or more light emitting components disposed on or within the brush head 1116. For example, as shown in FIGS. 11 and 12, the brush head includes a first light emitting element 1175 and a second light emitting element 1185. In one embodiment the first light emitting element 1175 is disposed within the center of the first bristle holder 1120, and particularly concentrically disposed therein. As shown in FIG. 12, the first light emitting element 1175 can also be disposed under the first bristle holder 1120. This configuration is described in greater detail herein. Also disposed within the brush head 1116 is the second light emitting element 1185. The second light emitting element 1185 can be disposed within the interior of the brush head 1116 as best shown in FIG. 12. However, as illustrated in FIG. 11, both light emitting elements 1175 and 1185 can be exposed or viewable along the outer face of the brush head 1116. The light emitting element(s) can also be disposed between a first bristle holder 1120 and second bristle holder 1122 as shown in FIG. 11. The second bristle holder 1122 can comprise a cut-out 1127. This cut-out area can allow the light emitting element 1185 to be exposed, and light shining from the light emitting element is not obstructed by the bristle holder 1122. The bristle holder can also comprise a transparent and/or translucent material which allows light to pass through the bristle holder. Additionally, the areas above the light emitting element can be substantially free of bristles. This second bristle holder 1122, can be stationary or can undergo motion, including, but not limited to, oscillation, rotation, reciprocation, and/or any combination thereof. Furthermore, if this second bristle holder undergoes motion, the cut-out 1127 area of the bristle holder can also move. This cut out 1127 can be arranged such that the light emitting element is partially, completely, or not at all covered by the bristle holder when the bristle holder undergoes motion. In another embodiment of the present invention as shown in FIG. 6a the light emitting element 475 is disposed partially underneath a first bristle holder 420 that is disposed in the center of the head 416 of the toothbrush, and partially underneath a second bristle holder 421 disposed on the portion of the head 416 that is proximal to the neck 414 of toothbrush 400. The bristle holder(s) can comprise a translucent and/or transparent material thereby allowing light to pass through the bristle holders even if the light emitting element is completely or partially covered by the bristle holder. Additionally, a third bristle holder 422 can be disposed on the distal end of the head 416 of the toothbrush, and a light emitting element 475 can be disposed partially underneath the first bristle holder 420 and partially underneath the third bristle holder 422.

Figure 7B:
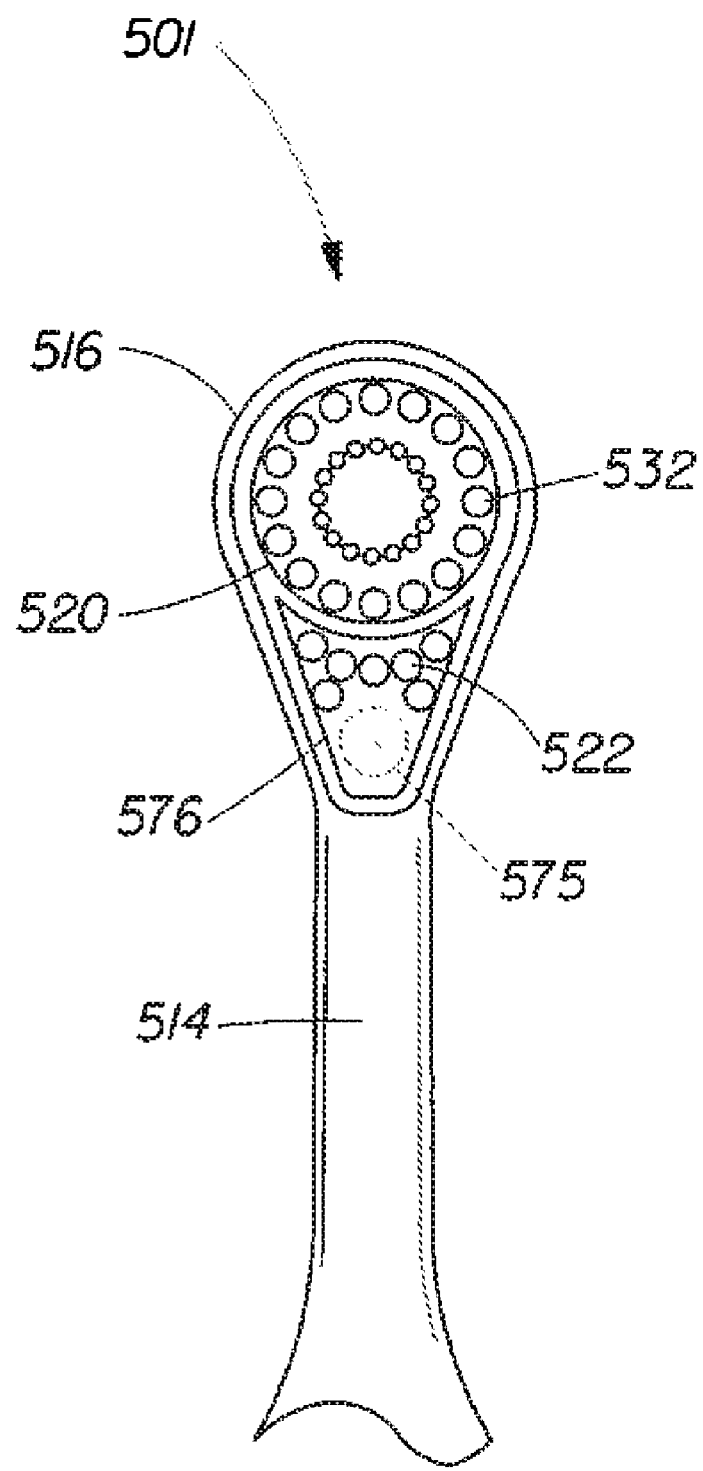
FIG. 7b is a partial front elevational view of a head and neck of yet another embodiment of the present invention.

In other embodiments, the light emitting element can be disposed on, in or under the second bristle holder located on a portion of the toothbrush head proximal to the neck, as shown in FIGS. 7, 7b, and 8. FIG. 7 illustrates a toothbrush embodiment 500 having a head 516 and a neck 514. It will be appreciated that the neck 514 extends between the head 516 and a handle of the toothbrush (not shown). Disposed on the head 516 is a single moving bristle holder 520 having a plurality of bristle tufts 532 disposed thereon. Disposed on a second bristle holder 534 is a light-emitting element 575. The toothbrush 500 can include a plurality of static bristles 522 disposed on the second bristle holder 534. The light emitting element 575 extends through the second bristle holder 534, and the area above the light emitting element 575 is substantially free of bristles. FIG. 7b illustrates an embodiment of the toothbrush 501 having a light emitting element 575 disposed underneath a second bristle holder 576 located on a portion of the head proximal to the neck 514. This bristle holder 576 is translucent and/or transparent, thereby allowing light to shine through the bristle holder 576.

FIG. 8 depicts a portion of a toothbrush 800 having a head 816 and a neck 814. The head 816 has a first bristle holder 820 that moves and a second bristle holder 822 that is fixed or stationary. Both bristle holders have light-emitting elements 875 disposed thereon. The first bristle holder 820 has a plurality of bristle tufts 832 that encircle the light-emitting element 875 disposed thereon, and the second bristle holder 834 has a plurality of bristle tufts 822 that encircle the light-emitting element 875 disposed thereon. The light emitting element 875 extends through the second bristle holder 834, and the area above the light emitting element 875 is substantially free of bristles.

Figure 13:
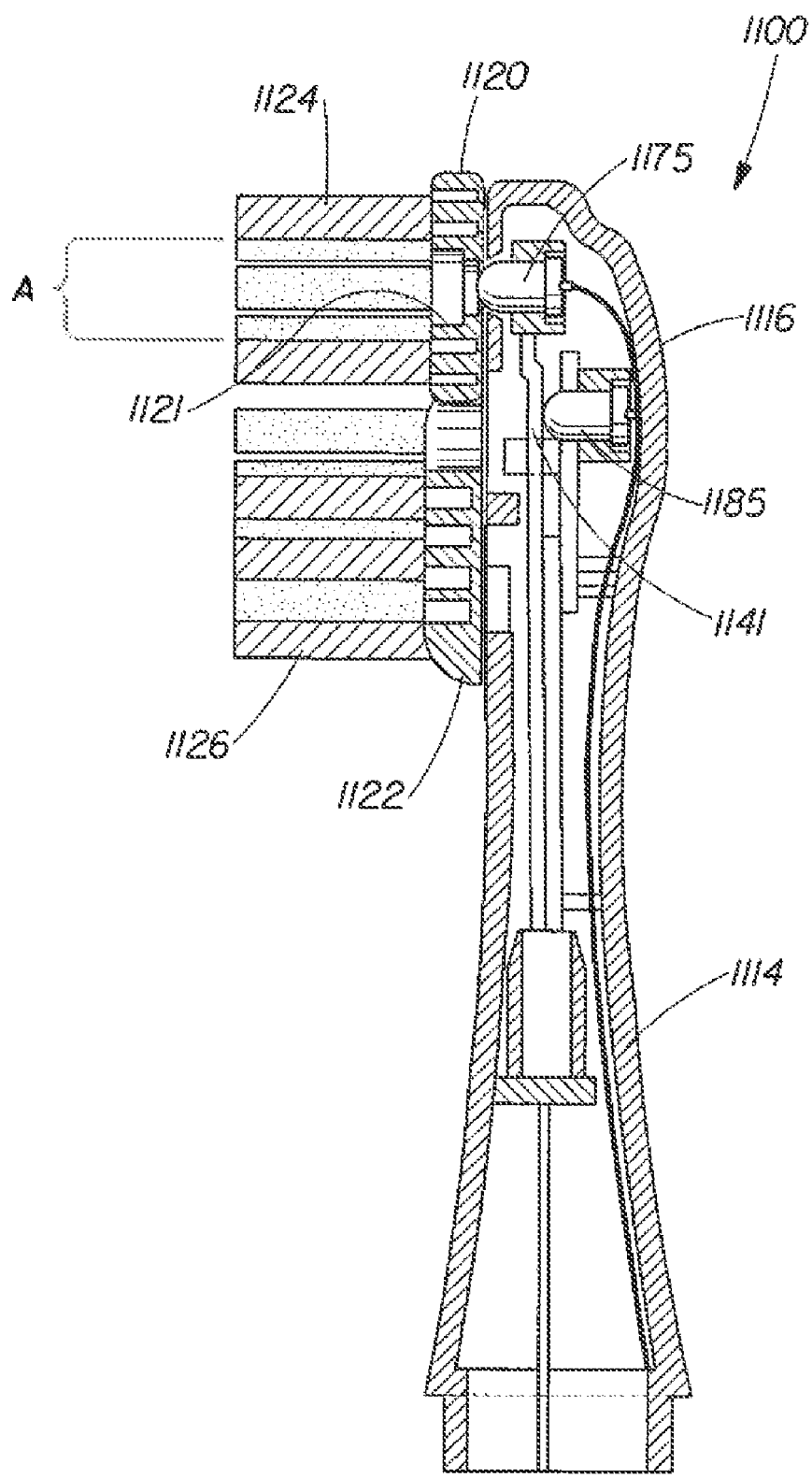
FIG. 13 is a cross-sectional side elevational view of the embodiment shown in FIG. 10.

In another embodiment of the toothbrush 1100, shown in FIG. 11, the first light emitting element 1175 is aligned with a region defined along the first bristle holder 1120 that is substantially free of any bristles. Specifically, it can be seen that the first light emitting element 1175 is generally disposed underneath the first bristle holder 1120, and accessible through an aperture 1121 defined in the bristle holder 1120. Furthermore, the first light emitting element 1175 can also be positioned such that light emitted from that element is unobstructed as it passes through the first bristle holder 1120 and past the plurality of bristles 1124 extending from the first holder 1120. Generally, the bristles 1124 are arranged about the perimeter of the first bristle holder 1120 so as to form a circular region of bristles, and particularly, to form a concentric ring about the first light emitting element 1175. The remaining region above the outer face of the first bristle holder 1120 which is substantially free of any bristles is shown in FIG. 13 as region A, which is generally cylindrical in shape. There it can be seen that the first light emitting element 1175 is concentrically disposed within region A.

FIG. 13 also illustrates the manner of mounting and/or engagement between the first light emitting element 1175 and the first bristle holder 1120. The first bristle holder 1120, can rotate or oscillate directly upon the light emitting element 1175. That is, in certain embodiments, the light emitting element 1175 or a component of that element such as a lens, cap, cover, shield, or the light emitting element itself, can provide the contacting surface and/or pin upon which the bristle holder 1120 rotates or oscillates. The aperture 1121 defined in the holder 1120 can be sized and configured so as to promote the movement of the holder 1120 about the element 1175. For example, the aperture can have a diameter slightly less than a maximum diameter of an element 1175 having a dome or cone-shaped tip such that the tip of the element partially extends within the aperture 1121. Alternatively, the aperture 1121 can be sized and configured such that it has a diameter slightly greater than the diameter of the light emitting element 1175 so that the element 1175 extends well into the aperture 1121, or entirely through the aperture 1121. In this latter configuration, the light emitting element serves as an axis for the oscillating or rotating bristle holder 1120.

Referring further to FIG. 13, the toothbrush 1100 also comprises a second, optional light emitting element 1185 generally disposed within the interior of the head 1116 of the toothbrush. The second element 1185 primarily serves to provide light for other transparent, translucent, or open regions of the toothbrush, and particularly in the region of the head 1116. Either of the light emitting elements 1175 and/or 1185 can be incorporated within a receiving or mounting structure within the head 1116, such as a pillar that defines a hollow region sized to accommodate the element.

Figure 23:
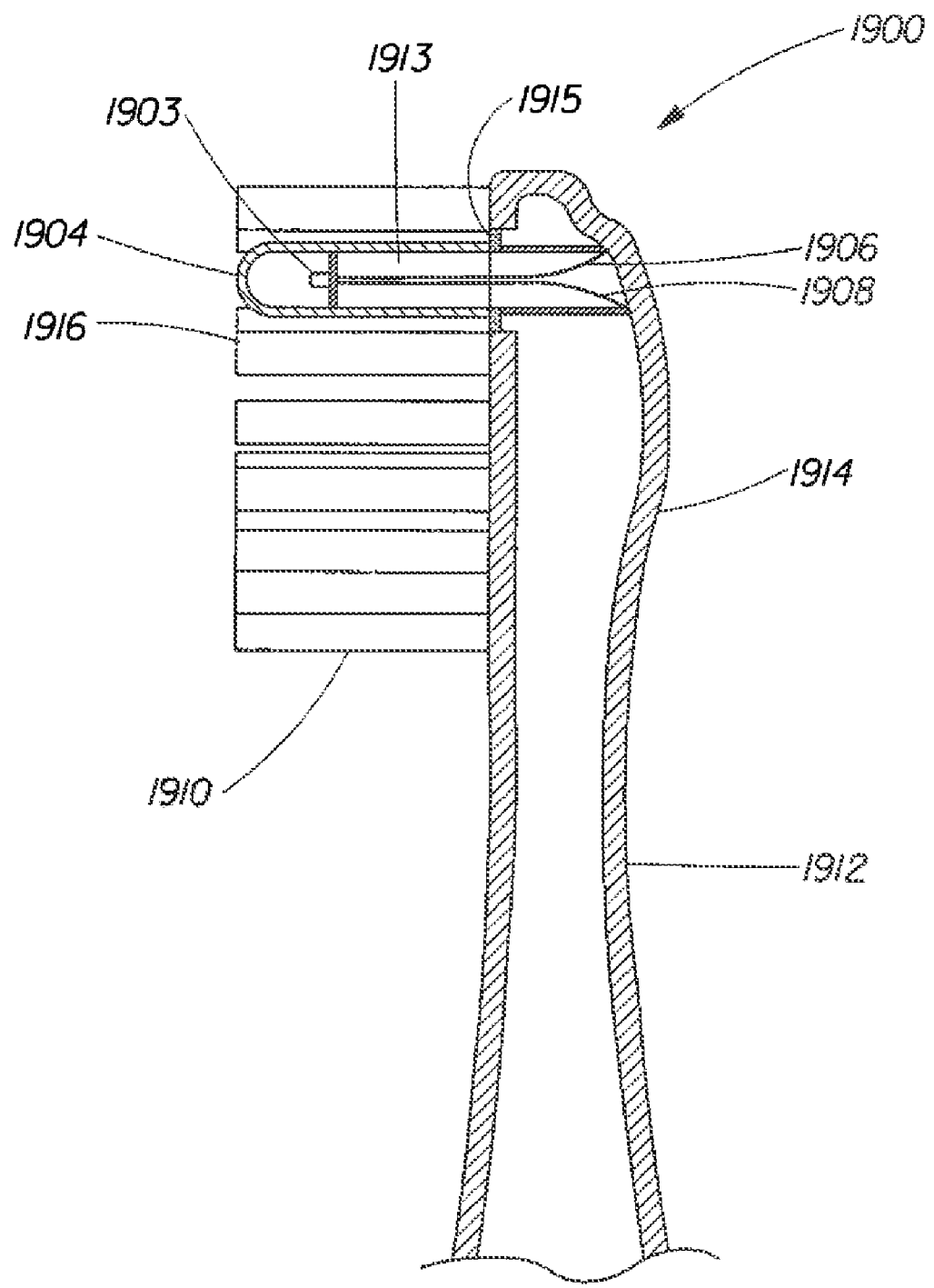
FIG. 23 is a cross-sectional side elevational view of an embodiment of the electric toothbrush of the present invention.

A light emitting element, such as a light emitting diode, comprises a light emitting substrate, the location where the light is generated, and a lens, the location from which the light emits. In one embodiment of the present invention, as shown in FIG. 22, a light emitting element is disposed on the head of the toothbrush such that the light emitting substrate 1902 is below and/or flush with the top surface 1915 of the head of the toothbrush. Top surface 1915 can be bristle bearing. However, the location from which the light emits, i.e. the lens 1904, extends from the top surface 1915 of the toothbrush to the distal ends 1916 of the bristles 1910 extending from said top surface 1915. The lens 1904 can comprise an elastomeric material. The elastomeric material can be transparent and/or translucent. During use, the lens comprising an elastomeric material can massage the gums and further assist with the cleaning of the oral cavity. The surface of the lens can comprise ridges, or the lens can be smooth. Alternatively, as shown in FIG. 23, the light emitting substrate 1903 can be disposed within or on the top of a pillar 1913 which extends above the top surface 1915 of the head of the toothbrush and the lens 1904 extends to the distal ends 1916 of the bristles 1910. In both FIGS. 22 and 23 leads 1906 and 1908 run from the light emitting element down the length of the pillar 1913 to the head 1914, and then the leads run down the length of the neck 1912 and handle (not shown) to connect to the power source (not shown).

Figure 25:
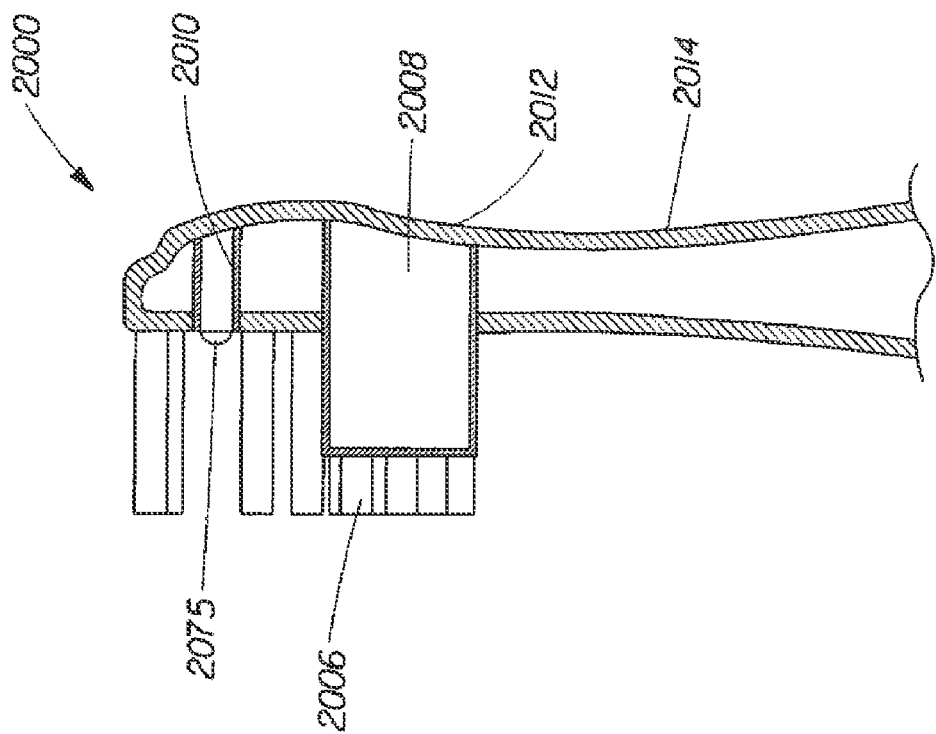
FIG. 25 is a cross-sectional side elevational view of an embodiment of the head and neck of an electric toothbrush of the present invention.
Figure 24:
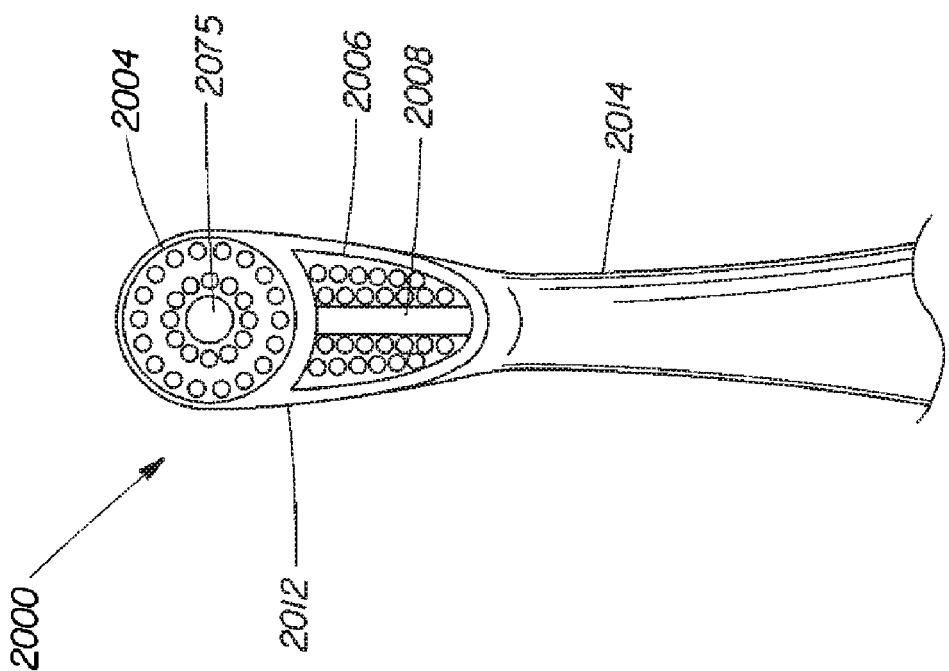
FIG. 24 is a front elevational view of an embodiment of the head and neck of an electric toothbrush of the present invention.

In another embodiment of the toothbrush, as shown in FIGS. 24 and 25 two electrically powered elements are disposed on the head 2012 of the toothbrush 2000. One element is a light emitting element 2075 disposed in a pillar 2010 and serves as the center pin for oscillating bristle holder 2004. The second electrically powered element is an ultra-sound emitting element 2008 disposed in a bristle holder 2006 proximal to the neck 2014 and/or handle (not shown) of the electric toothbrush. However, it is contemplated that the ultra-sound emitting element can also be disposed at the distal end of the toothbrush above the light emitting element, or the ultrasound emitting element could be partially disposed on the neck of the electric toothbrush.

Figure 27:
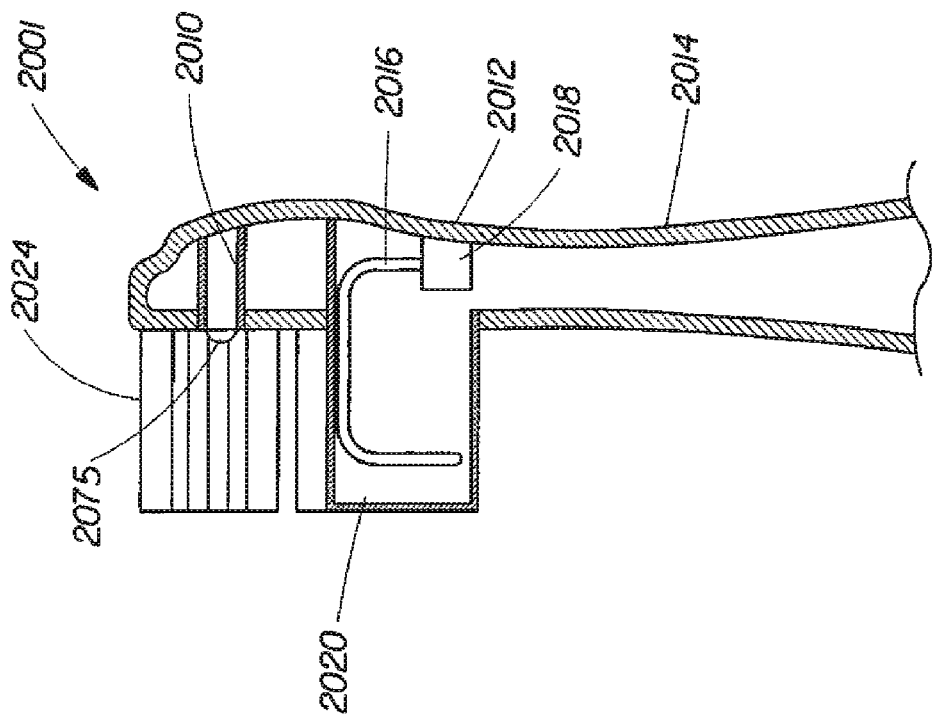
FIG. 27 is a cross-sectional side elevational view of an embodiment of the head and neck of an electric toothbrush of the present invention.
Figure 26:
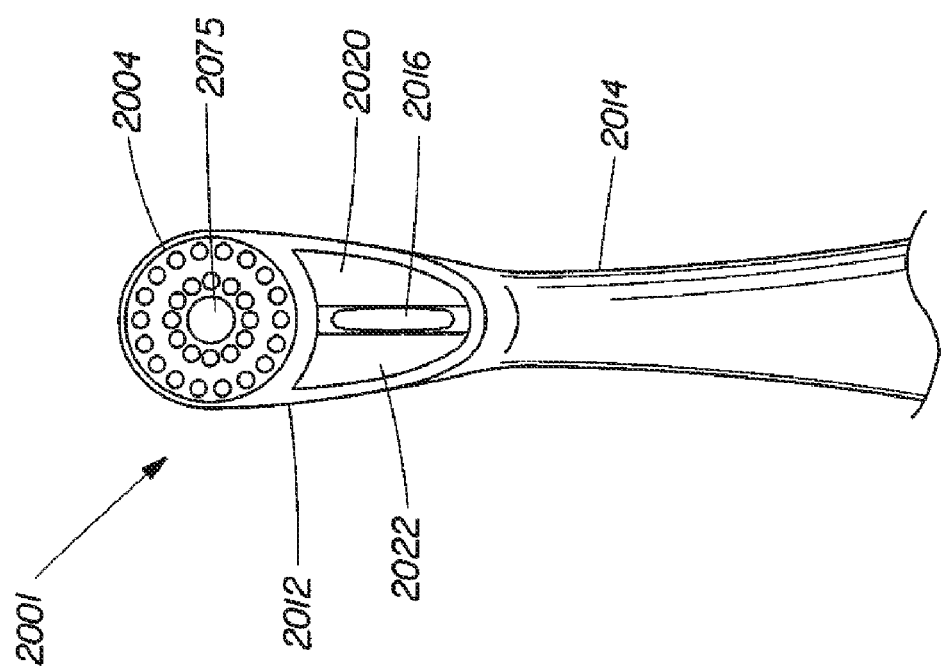
FIG. 26 is a front elevational view of an embodiment of the head and neck of an electric toothbrush of the present invention.
Figure 30:
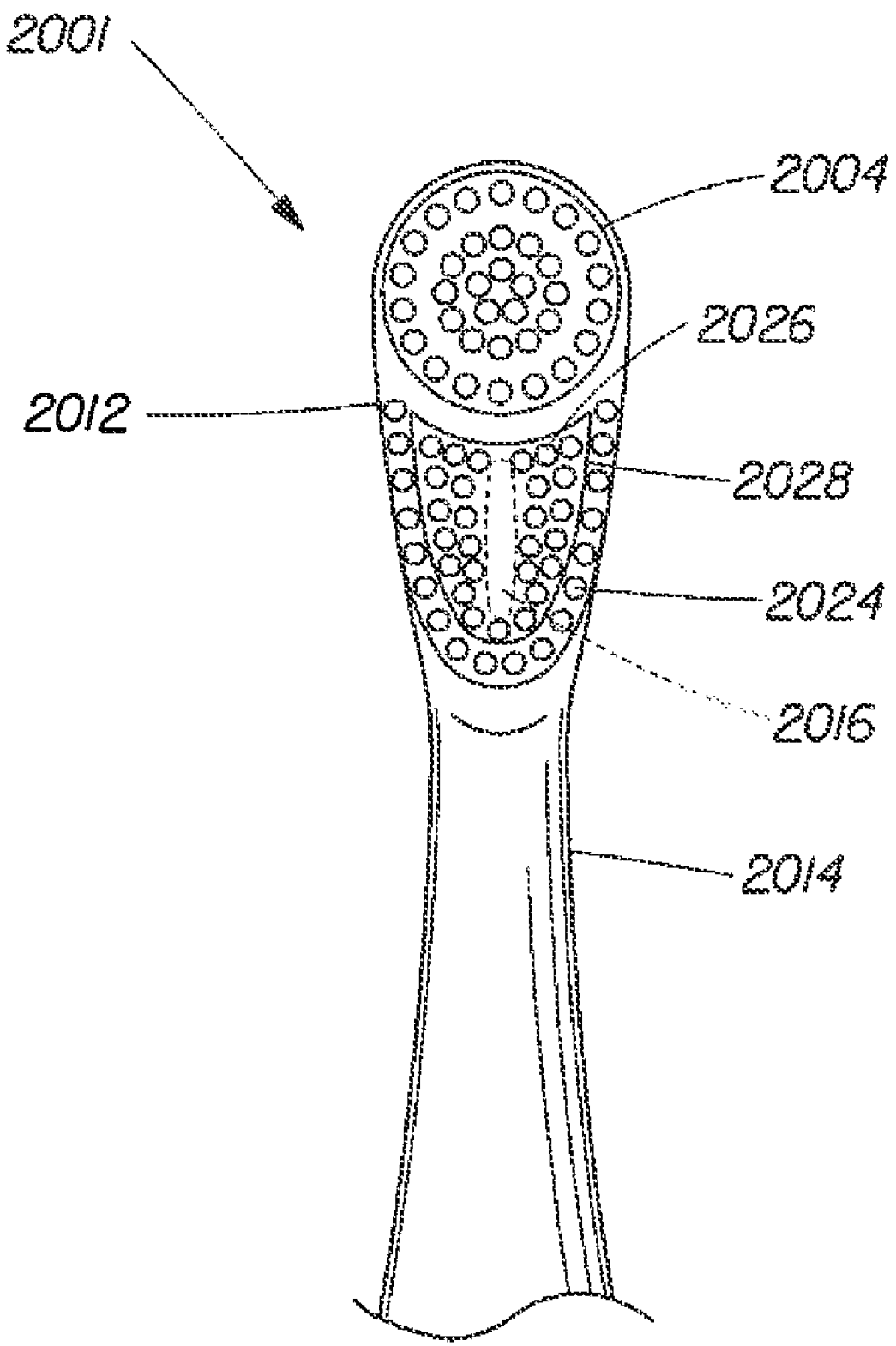
FIG. 30 is a front elevational view of an embodiment of the head and neck of an electric toothbrush of the present invention.

Another embodiment of the toothbrush 2001 comprising an ultra-sound emitting element is shown in FIGS. 26 and 27. The ultrasound emitting element comprises an ultrasonic transducer 2018 and an ultrasonic horn 2016. The ultrasonic transducer 2018 is disposed on the head of the toothbrush 2012 and the ultrasonic horn 2016 extends from the ultrasonic transducer 2018 towards the surface of the toothbrush which contacts the teeth. In this embodiment the teeth are contacted by walls 2020, and 2022. These walls can be elastomeric and/or non-elastomeric and extend above and/or surround the ultrasonic horn 2016 thereby creating a space between the ultrasonic horn and the teeth. This space serves as a safety precaution, preventing the ultrasonic horn from contacting the teeth. These walls can be a static bristle plate 2028, and bristles 2026 can be disposed thereon (as shown in FIG. 30). The walls can vibrate, and gel placed on top of the walls can transmit the vibration between the ultrasonic element and the surfaces of the teeth. Additionally, the bristles 2024 can surround the walls and/or the ultrasonic element. Bristles 2024 and 2026 surrounding the ultrasonic horn 2016, and disposed on the static plate 2028 disposed around the ultrasonic horn 2016 can vibrate as a result of the ultrasonic emissions from the ultrasonic element. The elastomeric walls 2020 and 2222, including the static plate 2028, serve to trap an oral care composition between the elastomeric walls and the ultrasonic horn. When this embodiment of the toothbrush is used to brush the teeth, this oral care composition comes into contact with the teeth, thereby aiding the transmission of ultrasonic waves from the ultrasonic horn to the teeth. This oral care composition can be a gel. The ultrasonic element can be used in combination with a light emitting element 2075, which can also disposed on the head of the toothbrush.

Figure 29:
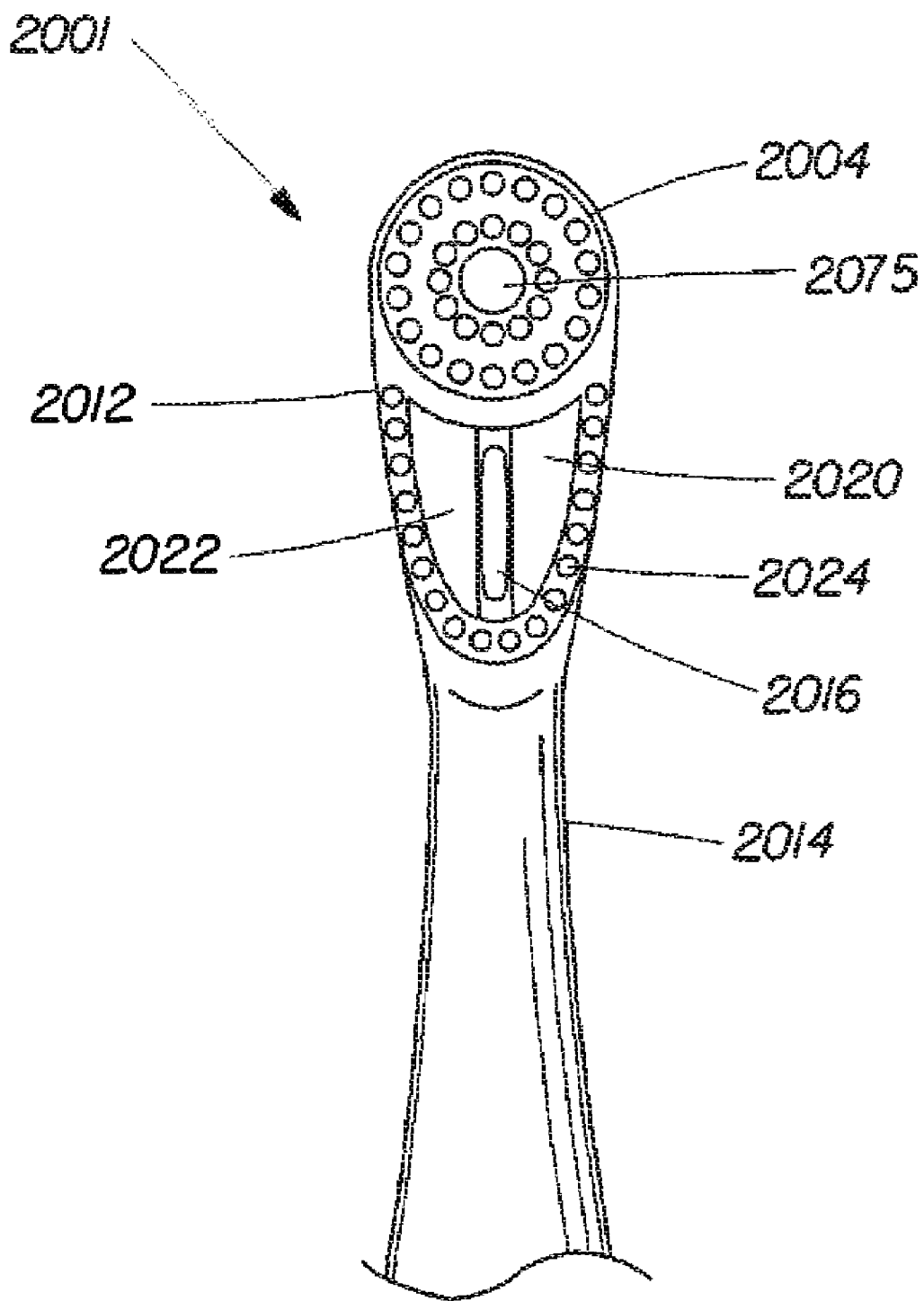
FIG. 29 is a front elevational view of an embodiment of the head and neck of an electric toothbrush of the present invention.

In embodiment 2001 of the toothbrush the oscillating bristle holder 2004 surrounding the light emitting element 2075 can be the only movable surface of the head of the toothbrush comprising bristles 2024. The ultrasonic element disposed on the head of the toothbrush proximal to the handle 2014 can serve to clean the teeth. An ultra-sonic element has superior teeth cleaning properties. Bristles 2024 can be disposed on the static non-moving portions of the head of the toothbrush (as shown in FIG. 29).

Figure 28:
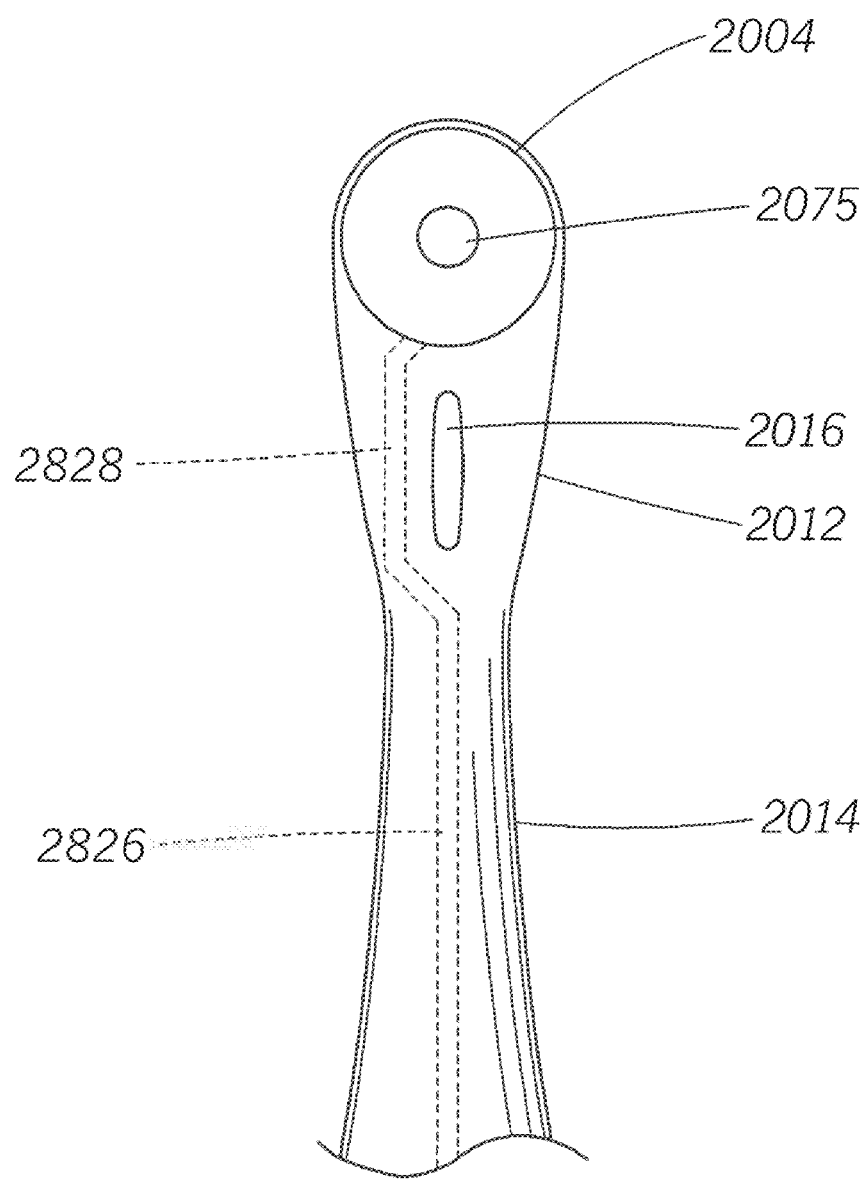
FIG. 28 is a front elevational view of an embodiment of the head and neck of an electric toothbrush of the present invention.

The drive shaft 2826 of the embodiments of the toothbrush 2000 and 2001 operatively connects the oscillating bristle holder 2004 to the motor (not shown) via the neck 2014 and can be designed to bypass the ultra-sonic element 2008 or the ultra-sonic horn 2016 and ultra-sonic transducer 2018 disposed on the head 2012 of the toothbrush as shown in FIG. 28. The drive shaft 2826 can have a lateral displacement portion 2828 which bypasses the ultra-sonic horn 2016 and ultrasonic transducer 2018 and then extends along the head of the toothbrush to the oscillating bristle holder 2004. This same design will also allow a drive shaft to bypass an ultrasonic element 2008.

A toothbrush made according to the present invention can be used with a composition. However, if such a toothbrush is used in combination with a composition, including, but not limited to, a tooth whitening composition, the composition can build up in the areas around the light emitting element; such as the cut-out areas, the apertures through which the light shines and/or through which the light emitting element extends, and/or open spaces surrounding the light emitting element(s). This build up can reduce the quality and/or quantity of light emitting from the head of the toothbrush. To minimize the amount of composition build up in the areas surrounding and on the light emitting element(s), drains and/or channels can be provided on and/or within the head of the toothbrush. FIG. 11 illustrates a toothbrush head provided with channels 1125 and 1123, to facilitate drainage of the composition from the area around the light emitting elements 1175 and 1185. Channel 1125 can be formed by the end surface of a first bristle holder 1120 and the end surface of a second bristle holder 1122. Alternatively the channels can be disposed on, within, and/or under the bristle holder. Generally, the channels begin at the light emitting element, such as 1185, and extend to the side surfaces 1129 of the head 1116 of the toothbrush. Additionally, if the bristle holder 1122 reciprocates, the compositions within the channel 1125 can be agitated, which can increase the flow of the compositions away from the light emitting element. Channels can also be provided on the first movable bristle holder 1120. These channels 1123 extend from the surfaces of the bristle holder closest to the light emitting element 1175 towards the ends surface 1131 of the movable bristle holder 1120. These channels can be grooves in the bristle holder. If movable bristle holder 1120 oscillates, the centrifugal force resulting from the oscillation can increase the level of composition which is directed away from the light emitting element 1185 towards the end 1131 of the bristle holder 1120. The channels can be any shape which allows compositions to flow away from the light emitting element. Additionally, channels 1130, 1132, 1133, and 1134 can extend through the head 1116 of the toothbrush, allowing water to flow out the back of the toothbrush as shown in FIG. 11a. The channels can be greater than about 0.5, 1, 1.5, 2, 2.5, 3 mm and less than about 3, 2.5, 2, 1.5, 1 mm in width; and greater than about 2, 3, 4, 5, 6, 7, 8, 9, 10, 15, 20, 25, mm and less than about 30, 25, 20, 15, 10, 9, 8, 7, 6, 5, 4, 3, 2 mm in length; and a depth of greater than about 0.5, 1, 1.5, 2, 2.5, 3 mm and less than about 3, 2.5, 2, 1.5, 1 mm. The channels can also serve to dissipate heat generated by the electrically powered element disposed on the head of the toothbrush.

Figure 14:
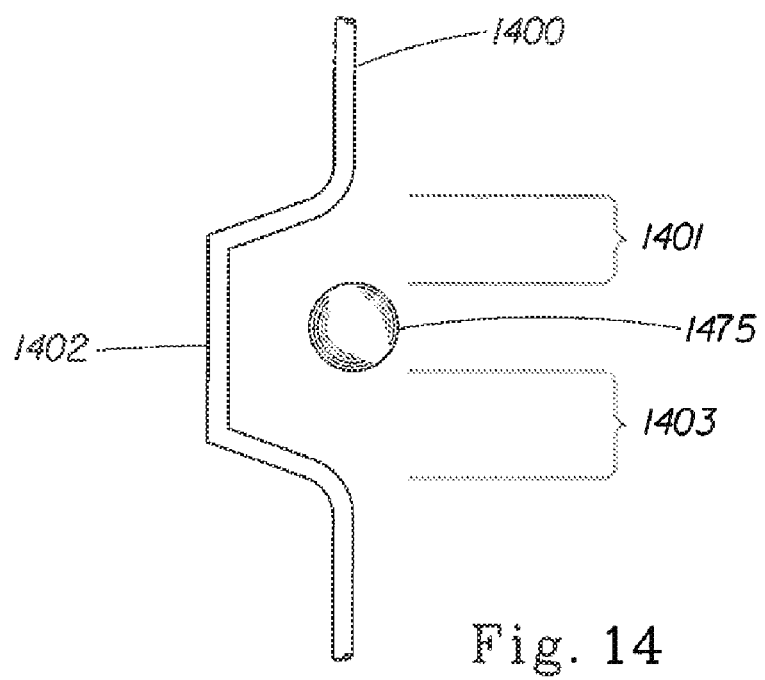
FIG. 14 is a partial front elevational view of an embodiment of a drive shaft of a toothbrush made according to the present invention.
Figure 15:
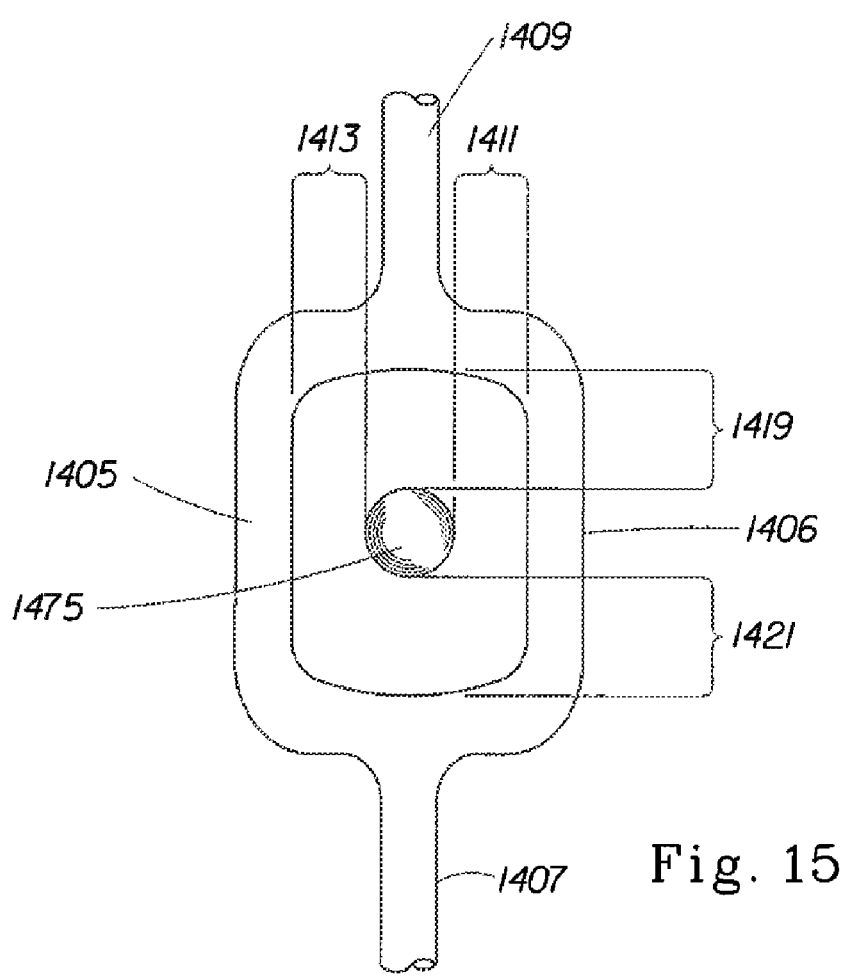
FIG. 15 is a partial front elevational view of an embodiment of a drive shaft of a toothbrush made according to the present invention.

If a light emitting element is incorporated into or located distal to the movable bristle holder no modification of the drive shaft is necessary. However, disposing the light emitting element in a region between a movable bristle holder and the motor, may interfere with the operation of the drive shaft preventing an operative connection between the drive shaft and the movable bristle holder. Therefore, to impart motion to the movable bristle holder, modifications can be made to the drive shaft to facilitate the operative connection between the movable bristle holder and the drive shaft. The drive shafts shown are generally suitable to allow for placement of a light emitting element along the length of the toothbrush that corresponds to the position of the drive shaft. However, for simplicity's sake, the light emitting element will be described as placed on and/or in the head of the toothbrush. The operative connection between the drive shaft and the movable bristle holder can be achieved by a drive shaft that bypasses the light emitting element, a drive shaft that serves as a base or support for the light emitting element, a drive shaft that passes over the light emitting element wherein at least a portion of the drive shaft is transparent to the emitted light, a drive shaft that passes underneath a light emitting element, and/or modifying a light emitting element such that the drive shaft becomes a part of the light emitting element. FIGS. 14-15 illustrate drive shafts which bypass the light emitting element, and therefore allow the drive shaft to operatively connect to a movable bristle holder when a light emitting element is disposed between the drive shaft and the movable bristle holder (such as shown in FIG. 7). Furthermore, if the drive shaft rotates, oscillates, gyrates, orbits and/or moves in a conical fashion the drive shaft can be flexible, bending around the light emitting element when the drive shaft is operating. If the drive shaft reciprocates, the drive shaft can be flexible or inflexible so long as the drive shaft does not contact the light emitting element while operating.

FIG. 14 illustrates a drive shaft 1400 for use in an electric toothbrush, comprising a lateral displacement portion 1402 that bypasses the light emitting element 1475. This embodiment of the drive shaft can operatively connect the motor (not shown) to the movable bristle holder (not shown) and bypass the light emitting element 1475 which can be disposed on any portion of the head of the toothbrush. The lateral displacement portion 1402 can be any shape or size necessary to bypass the light emitting element such that the drive shaft does not contact the light emitting element during operation. The shape and size of the lateral displacement portion 1402 can result in spaces 1401 and 1403 which are of sufficient size that the drive shaft does not contact the light emitting element while operating. The size of theses spaces can vary depending on the shaft motion, and the distance the shaft moves. In one embodiment, where the drive shaft reciprocates, the spaces 1401 and 1403 can be greater than about 0 and less than about 5 mm.

FIG. 15 illustrates a drive shaft that encircles the light emitting element that is disposed on the head of an electric toothbrush. Drive shaft 1407 splits into two lateral displacement portions 1405 and 1406, the lateral displacement portions encircle the light emitting element 1475 and then the lateral displacement portions rejoin to form the single drive shaft 1409. The drive shaft can operate without contacting the light emitting element. The spaces 1419 and 1421 should be sufficient such that the drive shaft does not contact the light emitting element while operating. Additionally, the spaces 1411 and 1413 should also be sufficient such that the drive shaft does not contact the light emitting element during operation. In an embodiment where the drive shaft reciprocates the spaces 1411 and 1413 can be greater than about 0, 0.5, 1, 1.5, 2, 3, 4, 6, 8, 10, 15, 20, 25, 30 mm and/or less than about 30, 25, 20, 15, 10, 8, 6, 5, 4, 3, 2, 1.5, 1, 0.5 mm, and the spaces 1419 and 1421 can be greater than about 0 and less than about 5 mm.

Figure 15A:
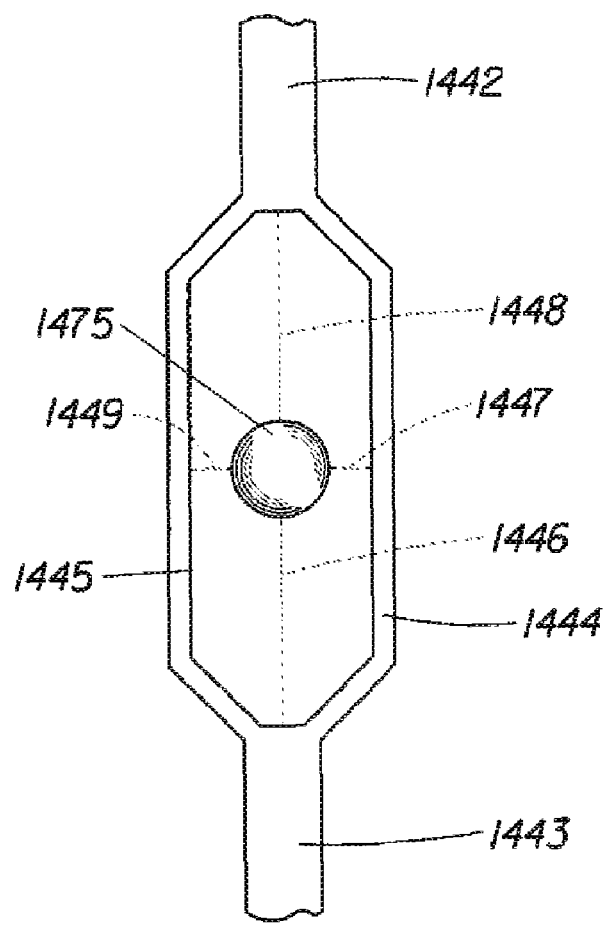
FIG. 15*a* is a partial front elevational view of an embodiment of a drive shaft of a toothbrush made according to the present invention.
Figure 15B:
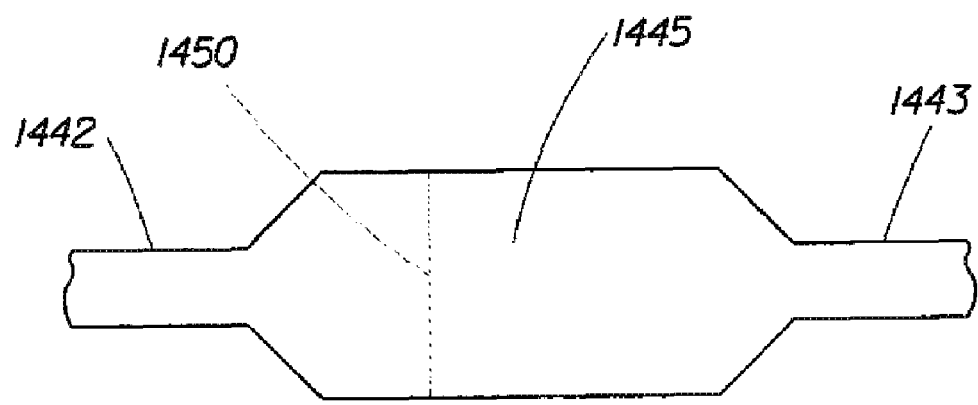
FIG. 15*b* is a partial side elevational view of the embodiment of the drive shaft shown in FIG. 15*a*.

The embodiment shown in FIG. 15 may result in a drive shaft having additional width. To minimize the increase of the width of the drive shaft resulting from the drive shaft splitting into two lateral displacement portions, the portions can be expanded in height rather than width as shown in FIGS. 15a and 15b. Drive shaft 1443 splits into two lateral displacement portions 1444 and 1445 and then rejoin to form drive shaft 1442. The drive shaft can operate without contacting the light emitting element. The spaces 1446, 1447, 1448, and 1449 should be sufficient such that the drive shaft does not contact the light emitting element while operating. In an embodiment where the drive shaft reciprocates the spaces 1446, 1447, 1448, and 1449 can be greater than about 0, 0.5, 1, 1.5, 2, 3, 4, 6, 8, 10, 15, 20, 25, 30 mm and/or less than about 30, 25, 20, 15, 10, 8, 6, 5, 4, 3, 2, 1.5, 1, 0.5 mm. The height 1450 of the arms 1444 and 1445 generates additional strength without resulting in a drive shaft having additional width. The height 1450 can be greater than about 0.2, 0.5, 0.75, 1, 1.5, 2, 3, 4, 5, 6, 7, 8, 9, 10, 13, 15 mm and/or less than about 15, 13, 10, 9, 8, 7, 6, 5, 4, 3, 2, 1, 1.5, 1, 0.75, 0.5, 0.2 mm.

Figure 16:
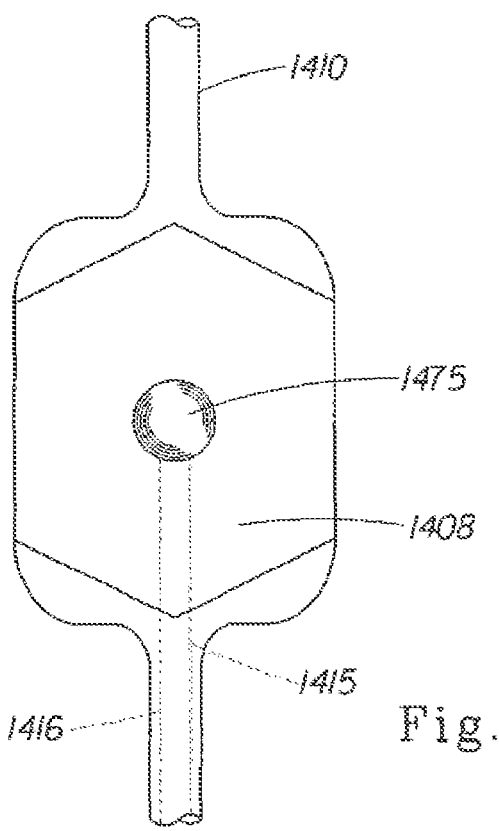
FIG. 16 is a partial front elevational view of an embodiment of a drive shaft of a toothbrush made according to the present invention.
Figure 17:
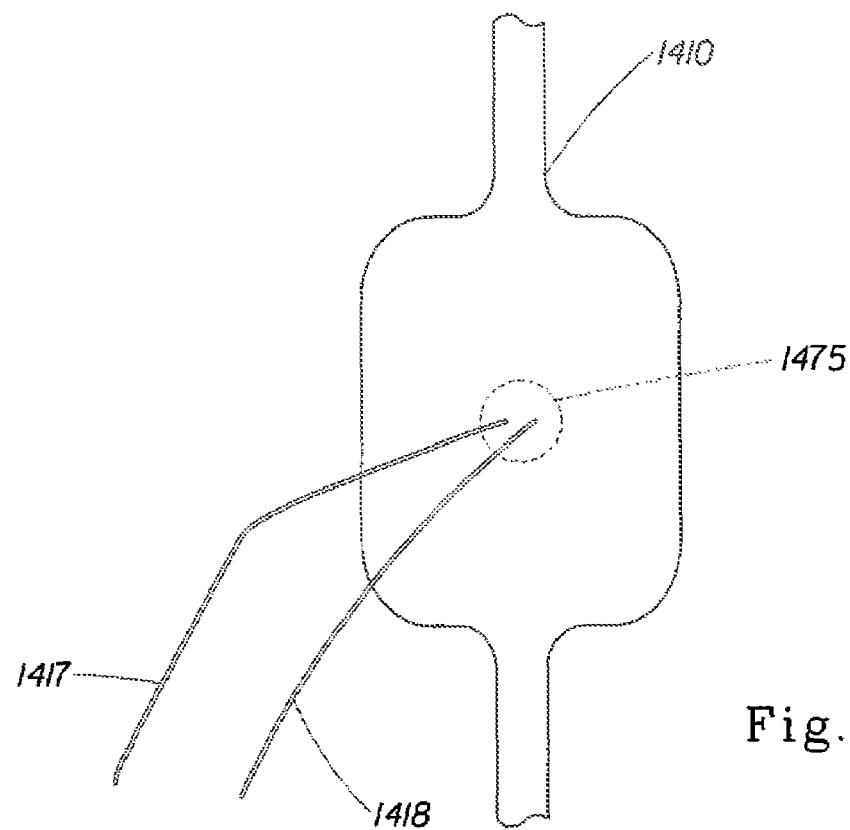
FIG. 17 is a partial back elevational view of an embodiment of a drive shaft of a toothbrush made according to the present invention.

FIG. 16-17 illustrates an embodiment of the drive shaft wherein the drive shaft serves as a support for a light emitting element. This drive shaft has a portion which is hollowed out such that a light emitting element can be disposed thereon. Drive shaft 1410 has a portion 1408 carved out and light emitting element 1475 is disposed thereon. As shown in FIG. 16, the leads 1415 and 1416 for the light emitting element can be incorporated into the drive shaft 1410, traveling the length of the drive shaft to the motor (not shown). Alternatively, as shown in FIG. 17, the leads 1417 and 1418 can exit the back of the drive shaft 1410 and travel along the head, neck and handle of the toothbrush to the motor (not shown).

As previously mentioned additional modifications can be made to drive shafts that rotate, oscillate, linearly reciprocate, gyrate, orbit, and/or move in a conical fashion to incorporate a light emitting element on and/or within the head of the toothbrush, including a transparent and/or translucent drive shaft, disposing the light emitting element underneath and/or above the drive shaft, and modifying the light emitting element such that the drive shaft becomes a part of the light emitting element.

Figure 10:
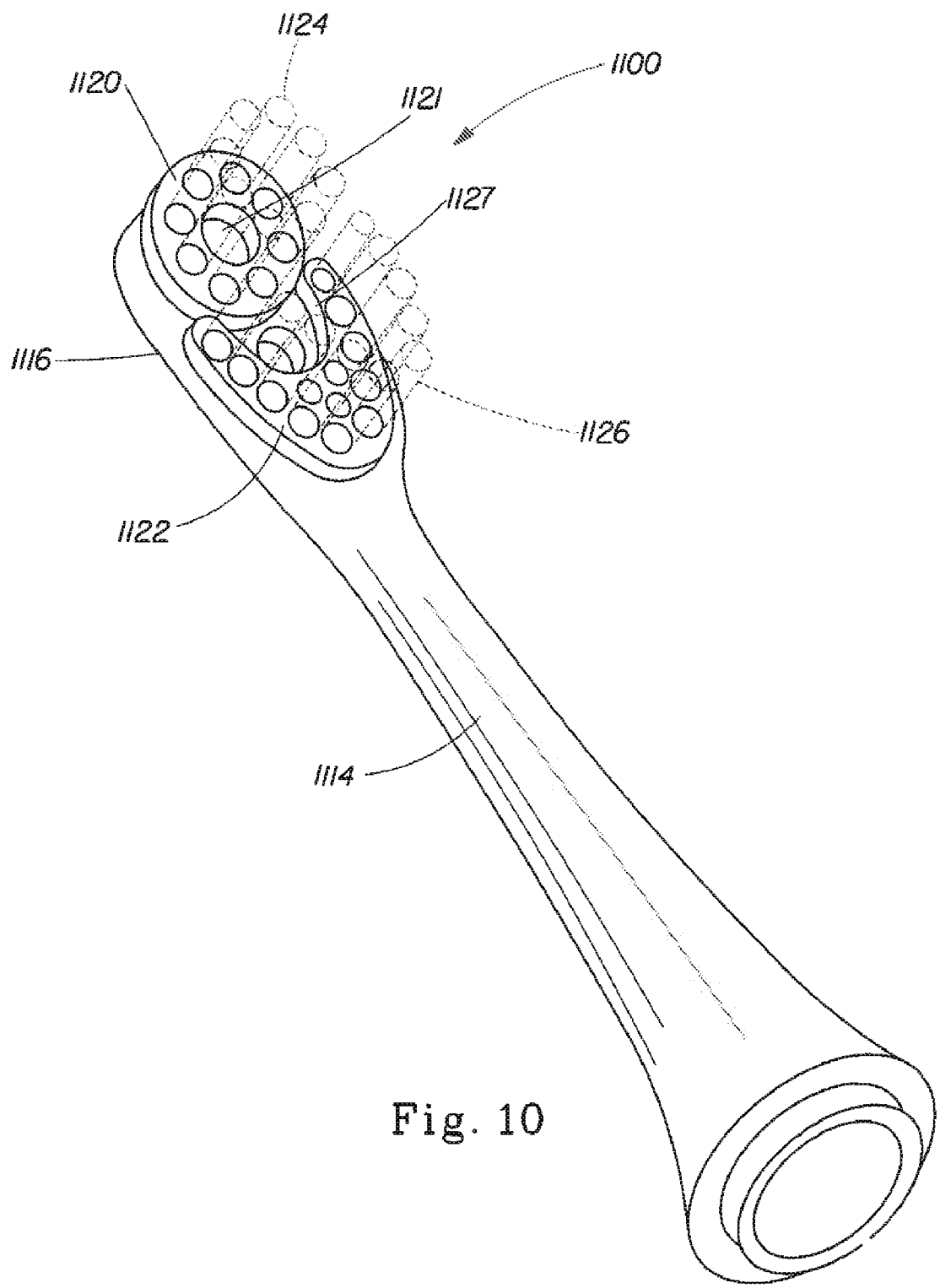
FIG. 10 is a perspective view of a head and neck of yet another embodiment of the present invention.

FIGS. 18-19 illustrates a drive shaft a drive shaft that passes underneath a light emitting element. Drive shaft 1500 has a transparent portion 1502 and portions 1504 and 1506 that can be either transparent and/or translucent or not transparent (i.e. opaque) and/or any combination thereof. The drive shaft is disposed between the light emitting element 1575 and the portion of the head of the toothbrush from which the light emits. At least a portion of the drive shaft 1500 can be transparent and/or translucent. This transparent and/or translucent portion of the drive shaft 1500 allows for light to pass from the light emitting element, through the drive shaft, and exit the head of the toothbrush. This transparent and/or translucent portion can be disposed above the light emitting element. The light emitting element can be disposed within the interior of the head of the toothbrush with the drive shaft traveling over top of the light emitting element such as light emitting element 1185 and drive shaft 1141 shown in FIG. 13. The portion of the head of the toothbrush from which light emits can be an aperture such as aperture 1121 as shown in FIG. 10. This aperture can be covered with a transparent and/or translucent material to prevent water from entering the head of the toothbrush while allowing light to emit from the head of the toothbrush.

In the embodiment illustrated in FIG. 19 the light emitting element 1675 is disposed underneath a drive shaft 1602 for an electric toothbrush. The drive shaft 1602 can be either transparent and/or translucent or not transparent and/or translucent (i.e. opaque). Reflectors 1600 and 1604 reflect the light emitting from the light emitting element around the drive shaft 1602, thereby allowing the light to emit from the head of the toothbrush. The drive shaft can comprise a reflective material, such as a reflective coating, which can serve to enhance the quality and/or quantity of light emitting from the head of the toothbrush.

FIG. 20 illustrates a light emitting element 1775 disposed between a drive shaft 1706 and the portion of the head of a toothbrush from which the light emits. Therefore, the drive shaft does not interfere with the light emitting from the light emitting element. Additionally, the leads 1704 and 1702 can be disposed in the walls of the head of the toothbrush and travel the length of the head and handle of the toothbrush to reach the motor (not shown). The light emitting element can be disposed on a support and/or a pillar through which the drive shaft passes to reach the movable bristle holder. Alternatively the light emitting element can be disposed on the head of the toothbrush such that no support and/or pillar is needed, and the drive shaft can pass underneath the light emitting element.

Figure 21:
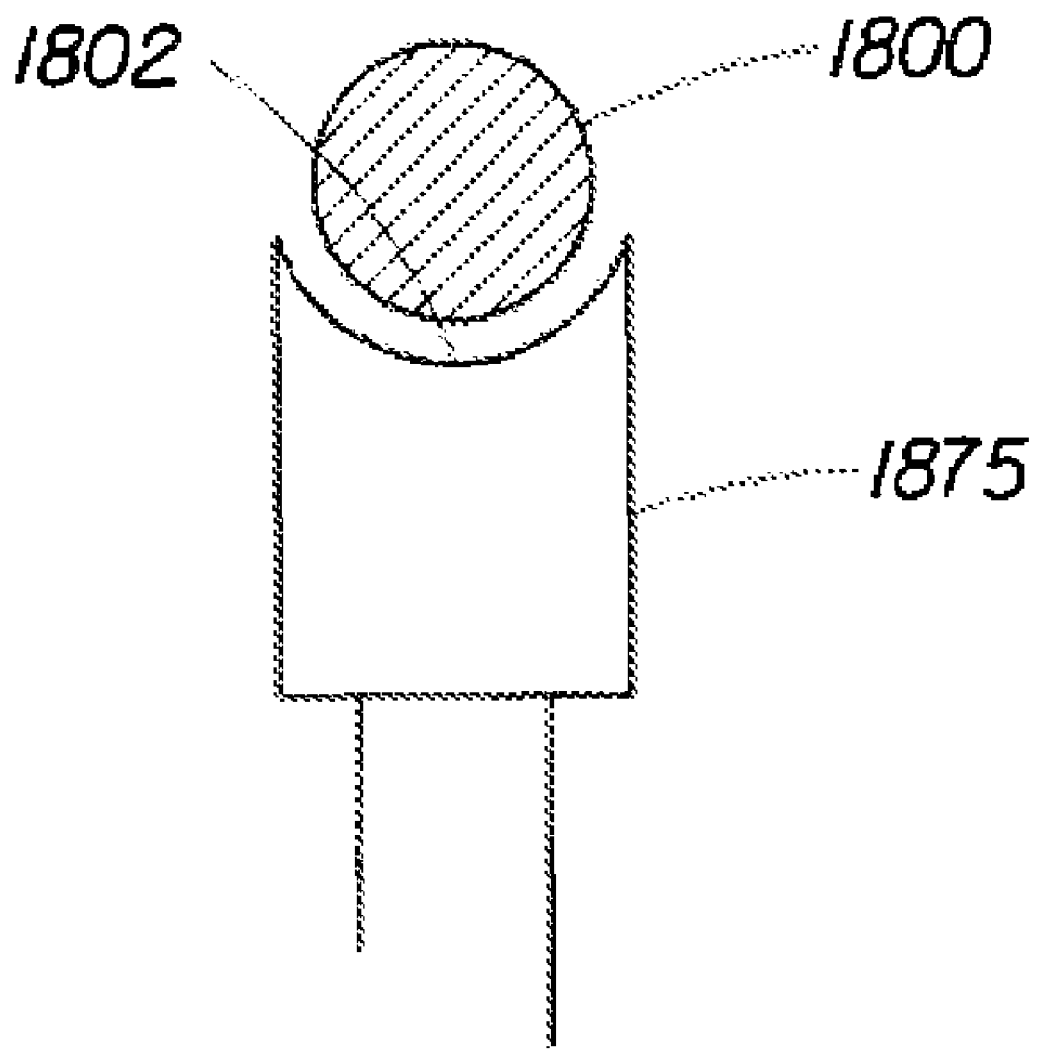
FIG. 21 is a cross sectional end view of a drive shaft and a light emitting element of a toothbrush made according to the present invention.

The light emitting element can also be modified, such that the drive shaft becomes part of the light emitting element. In FIG. 21 the light emitting element has a lens 1802 shaped to allow the drive shaft to sit within the light emitting element 1875. The drive shaft 1800 can be transparent and/or translucent, thereby allowing light to pass through the drive shaft to reach the portion of the head of the toothbrush from which light emits. Additionally, the drive shaft can include a design, material and/or shape that enhances the light emitting from the light emitting element. The light emitting element can be disposed on the interior of the head of the toothbrush such as light emitting element 1185 shown in FIG. 13.

A wide variety of light-emitting elements may be used with the present invention. The light emitting element can be a small, low power consumption, light emitting diode (LED) such as those commercially available under the designation Luxeon™ manufactured by Lumileds Lighting, LLC of San Jose Calif. Other commercially available light emitting units include those from American Opto Plus LED Corporation. The LED can operate from a relatively low voltage DC power supply, such as greater than about 0.5, 1, 2, 2.5, 3, 4, 5 volts and/or less than about 5, 4, 3, 2.5, 1.5, 1 volts. The light emitting element can have a diameter of greater than about 0.5, 1, 2, 3, 4, 5, 6, 7, 8, 10, 15, 20 mm and less than about 20, 15, 10, 8, 7, 6, 5, 4, 3, 2, 1 mm.

A voltage or current driver suitable for use with the present invention is the ZXSC310 Single or Multi Cell LED Driver manufactured by Zetex Semiconductors, Oldham, UK. Separate switches might be provided to separately active the light-emitting element and the motor. More than one light-emitting element might be provided. Light-emitting elements having different spectral, photometric, radiometric, and colormeteric characteristics (e.g., different dominant wavelengths, peak wavelengths, radiometric power, etc.) might be provided to accommodate multiple uses in a single electric toothbrush (i.e., the first light-emitting element might be adapted for use with a first light activated composition and the second light-emitting element might be adapted for use with a second light-activated composition).

As noted, it may be desirable in certain embodiments that the one or more movable bristle holders rotate, oscillate, or undergo motion; directly upon and contact a surface or region of the light emitting element. In these configurations, the present invention includes the use of a friction reducing layer or coating on the surface of the light emitting element which the bristle holder contacts. This layer or coating may also serve to reduce wear that might otherwise occur due to the contacting surfaces. A wide array of coating materials can be used including those known in the art and which are suitable for consumer healthcare appliances. Generally, such coatings are non-toxic and inert, durable, and depending upon the application, can be transparent or translucent. Examples of coatings suitable for use in the present invention include, but are not limited to Teflon, and silicone grease such as RT910T manufactured by Refrigeration Technologies, Nevastane 5 manufactured by Keystone Lubricants, and Nevastane SFG manufactured by Keystone Lubricants.

The present invention may be used in conjunction with nearly any tooth whitening composition, such as, but not limited to, the compositions described in U.S. Pat. Nos. 6,488,914; 5,851,514; 4,980,152; 3,657,413; 4,983,380; 5,084,268; 5,171,564; 5,376,006; 5,645,428; 5,713,738; RE 34,196; 5,122,365; 6,558,654; 6,555,020; 6,536,628; 6,533,582; 6,521,215; 6,514,543; 6,479,037; 6,447,757; 5,891,453; and 6,419,905. It is not necessary that the composition exhibit an enhanced whitening function upon exposure to light. Benefits may result simply from exposure of the tooth surface to light from the electrical toothbrush prior to application of the whitening composition. Furthermore, additional benefits may stem from greater brushing or cleaning efficacy resulting from illuminating the brushing area. In one aspect, the present invention relates to the use of the toothbrushes described herein during a whitening procedure wherein the whitening effect of the composition is enhanced or accelerated as a result of light and heat emitted from the light-emitting element of the electric toothbrush.

In some embodiments, it may be desirable that the toothbrush and whitening composition be "matched." That is, it is desirable that if the whitening composition exhibits enhanced or accelerated whitening function upon exposure to light of a certain wavelength or range of wavelengths, i.e. a band, then the wavelength of light emitted from the light emitting unit of the toothbrushes described herein is the same, or substantially so, as that certain wavelength. For example, if a particular whitening composition is identified for use with the toothbrushes described herein, and if that composition exhibits enhanced effects upon exposure to light of a peak wavelength of 430 nm to 470 nm, then the toothbrush to be used in conjunction with that composition emit light having a wavelength within the range of 430 nm to 470 nm.

The electric toothbrush can be packaged as a kit comprising one or more replaceable heads containing a light-emitting element. The heads can thus be replacements or individually assigned to different members of a family. Color distinction is thus often a part of the different heads in a kit. Although the handle is discussed as battery powered, the invention also includes other well known power supplies such as corded for outlet connection or rechargeable batteries and an associated brush holder/charger (not shown). The kit may further include one or more packaged, light-activated oral compositions, such as a packaged tooth whitening composition. Additionally, the kit can include other non-light activated oral care products and toothbrush heads that do not comprise a light emitting element.

Typical time periods for a brushing operation are generally greater than about 10, 20, 30, 45, 60, 90, 120, 150, 300, 360, 480 seconds and/or less than about 600, 480, 360, 300, 150, 120, 90, 60, 45 seconds.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiment of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush, comprising:
    a handle, a head, and a neck extending between the handle and the head; the handle having a hollow interior region, the hollow interior region comprising a motor and an electrical power source; the head comprising an ultrasonic transducer and a bristle field, wherein the ultrasonic transducer is in electrical communication with the electrical power source;
    an ultrasonic horn extending from the ultrasonic transducer;
    elastomeric walls which surround the ultrasonic horn; and a shaft operatively connected to the motor for moving the bristle field.

2. The electric toothbrush of claim 1, wherein a static bristle field surrounds the elastomeric walls.

3. The electric toothbrush of claim 1, wherein the shaft is rotatable.

4. The electric toothbrush of claim 1, wherein the head and neck are releasably attached to the handle.

5. The electric toothbrush of claim 1, wherein the shaft is disposed at least in part within the neck.

6. The electric toothbrush of claim 1, wherein the bristle field is attached to a movable bristle plate which oscillates.

7. The electric toothbrush of claim 1, further comprising a light emitting element.

8. The electric toothbrush of claim 7, wherein the head comprises the light emitting element.

9. The electric toothbrush of claim 7, further comprising a drain disposed adjacent the light emitting element.

10. The electric toothbrush of claim 1, wherein the head comprises a moving portion and a static portion, and wherein the bristle field is disposed on the moving portion.

11. The electric toothbrush of claim 1, wherein the shaft extends from the motor through the neck.

12. The electric toothbrush of claim 11, wherein the shaft comprises a lateral displacement portion.

* * * * *